United States Patent [19]
Collins et al.

[11] Patent Number: 5,986,070
[45] Date of Patent: *Nov. 16, 1999

[54] PRODUCTION OF BIOLOGICALLY ACTIVE NGF PROTEINS

[75] Inventors: Frank D. Collins; Jack Lile; Susan Becktesh, all of Boulder; Tadahiko Kohno, Louisvillle; Drizislav Mismer, deceased, late of Boulder, all of Colo., by Marijana Znidarcic, legal representative

[73] Assignee: Amgen Inc., Thousand Oaks, Calif.

[*] Notice: This patent is subject to a terminal disclaimer.

[21] Appl. No.: 08/918,101

[22] Filed: Aug. 27, 1997

Related U.S. Application Data

[63] Continuation of application No. 08/265,520, Jun. 24, 1994, abandoned, which is a continuation of application No. 08/087,912, Jul. 6, 1993, abandoned, which is a continuation of application No. 07/680,681, Apr. 4, 1991, abandoned, and a continuation-in-part of application No. 07/594,126, Oct. 9, 1990, Pat. No. 5,235,043, and a continuation-in-part of application No. 07/547,750, Jul. 2, 1990, abandoned, and a continuation-in-part of application No. 07/505,441, Apr. 6, 1990, abandoned.

[51] Int. Cl.$^6$ ...................................................... C07K 1/14
[52] U.S. Cl. .......................... 530/404; 530/412; 530/402
[58] Field of Search ..................................... 530/399, 402, 530/404, 412, 417–419, 422; 536/23.51; 435/69.1, 69.4, 71.1, 172.3, 849, 252.33

[56] References Cited

U.S. PATENT DOCUMENTS

| | | | |
|---|---|---|---|
| 4,421,685 | 12/1983 | Chance et al. | 260/112.7 |
| 4,451,396 | 5/1984 | DiMarchi . | |
| 4,511,502 | 4/1985 | Builder . | |
| 4,511,503 | 4/1985 | Olson et al. | 260/112 R |
| 4,512,922 | 4/1985 | Jones . | |
| 4,518,526 | 5/1985 | Olson . | |
| 4,599,197 | 7/1986 | Wetzel . | |
| 4,620,948 | 11/1986 | Builder et al. | 530/419 |
| 4,766,205 | 8/1988 | Ghosh-Dastidar . | |
| 4,873,312 | 10/1989 | Arakawa . | |
| 4,923,967 | 5/1990 | Bobbit et al. . | |
| 4,929,700 | 5/1990 | Halenbeck . | |
| 5,169,762 | 12/1992 | Gray . | |
| 5,169,764 | 12/1992 | Shooter . | |
| 5,180,820 | 1/1993 | Barde et al. | 536/23.51 |
| 5,210,185 | 5/1993 | Della Valle . | |
| 5,235,043 | 8/1993 | Collins et al. | 530/399 |

FOREIGN PATENT DOCUMENTS

| | | |
|---|---|---|
| 1220763 | 4/1987 | Canada . |
| 0 121 338 | 10/1984 | European Pat. Off. . |
| 0 329175 A1 | 8/1989 | European Pat. Off. . |
| 0 336 324 | 10/1989 | European Pat. Off. . |
| 0 361 830 | 4/1990 | European Pat. Off. . |
| WO 87/02985 | 5/1987 | WIPO . |
| 9103568 | 3/1991 | WIPO . |
| 9103569 | 3/1991 | WIPO . |
| WO 91/03568 | 3/1991 | WIPO . |
| WO 91/03569 | 3/1991 | WIPO . |

OTHER PUBLICATIONS

Sarmientos et al. (1989) Biotechnology 7:495.
Translation of Protein Molecules, Iwanami Shoten Co., pp. 99–129 (1985), Chapter 7.
Jaenicke et al., "Folding Proteins" in Protein Structure—A Practical Approach, Creighton, TE. ed., Oxford, pp. 191–223 (1990).
Scopes, Protein Purification—Principles and Practice, Springer–Verlag, NY, Table of Contents, pp. 33–35, 45–54, 93–99, 111,113, 199,208, 285,290 (1987).
Winkler, M.E. et al. J. Biol. Chem. 261:13838–43 (1986).
Van Snick, J. et al. Eur. J. Immunol. 18:193–197 (1988).
Hu and Neet (1988) *Gene* 70:57–65.
Kelley and Winkler (1990) *Genetic Engineering* 12:1–19, Ed. J.K. Setlow, Plenum Press, NY and London.
Leibrock et al. *Nature* 341:149–152 (1989).
Jones et al. *Proc. Natl Acad Sci USA* 87:8060–8064 (1990).
Hofer et al *Nature* 331: 261–262 (1988).
Barde et al. *EMBO J.* 1: 549–53 (1982).
Ernfors et al. *Proc. Natl Acad Sci* 87: 5454–5458 (1990).
Hufer et al *EMBO J.* 9:2459–2464 (1990).
Maisonpierre et al *Genomics* 10: 558–568 (1991).
Cleland et al. (1992) J. Biol. Chem. 267:13327.
Dicou et al. (1989) J. Neurosci. Res. 22:13.
Edwards et al. (1988) Molec. and Cell Biol. 8:2456.
Edwards et al. (1986) Nature 319:784.
Gonzalez and Damodaran (1990) J. Agric. Food Chem. 38:149.
Iwai et al. (1986) Chem. Pharm. Bull. 34:4724.
Knusel et al. (1991) PNAS 88:961.
Kohno (1990) Methods Enzymol. 185:187.
Leibrock et al. (1989) Nature 341:149.
Light (1985) Biotechniques 3:298.
Maisonpierre et al. (1990) Science 247:1446.
Ullrich et al. (1983) Nature 303:821.

*Primary Examiner*—Marianne P. Allen
*Attorney, Agent, or Firm*—Swanson & Bratschun LLC

[57] ABSTRACT

This invention describes processes for producing mature human members of the NGF/BDNF family of neurotrophic proteins that are fully biologically active. In addition, the gene encoding human BDNF and human BDNF are disclosed. A previously-unreported member of the NGF/BDNF family of neurotrophic proteins, NGF-3, has been identified and a portion of the gene encoding for the NGF-3 has been described.

14 Claims, 14 Drawing Sheets

FIGURE 1

```
ATG ACC ATC CTT TTC CTT ACT ATG GTT ATT TCA TAC TTT GGT TGC ATG AAG GCT GCC
 M   T   I   L   F   L   T   M   V   I   S   Y   F   G   C   M   K   A   A

CCC ATG AAA GAA GCA AAC ATC CGA GGA CAA GGT GGC TTG GCC TAC CCA GGT GTG CGG
 P   M   K   E   A   N   I   R   G   Q   G   G   L   A   Y   P   G   V   R

ACC CAT GGG ACT CTG GAG AGC GTG AAT GGG CCC AAG GAG TCA AGA GGC TTG ACA
 T   H   G   T   L   E   S   V   N   G   P   K   E   S   R   G   L   T

TCA TTG GCT GAC ACT TTC GAA CAC GTG ATA GAA GAG CTG TTG GAT GAC CAG AAA
 S   L   A   D   T   F   E   H   V   I   E   E   L   L   D   D   Q   K

GTT CGG CCC AAT GAA GAA AAC AAT AAG GAC GCA GAC TTG TAC ACG TCC AGG GTG ATG
 V   R   P   N   E   E   N   N   K   D   A   D   L   Y   T   S   R   V   M

CTC AGT CAA GTG CCT TTG GAG CCT CTT CTC TTT CTG GAG GAA TAC AAA
 L   S   Q   V   P   L   E   P   L   L   F   L   E   E   Y   K

AAT TAC CTA GAT GCT GCA AAC ATG TCC ATG AGG GTC CGG CAC GTC TCT GAC CCT GCC
 N   Y   L   D   A   A   N   M   S   M   R   V   R   H   V   S   D   P   A

CGC CGA GGG GAG CTG GTG AGC CTG TGT GAC AGT GGG ACG ATT AGT GAG TGG GTA GCA GAC
 R   R   G   E   L   V   S   L   C   D   S   G   T   I   S   E   W   V   A   D

AAA AAG ACT GCA GTG ATG TCG GGG TAC TTC ACA GTC CTT CTT GAA AAG CCC CAG GTC CCT
 K   K   T   A   V   M   S   G   Y   F   T   V   L   L   E   K   P   Q   V   P

GTA TCA AAA CAA CTG AAG CAA TAC AAA ATG ACC TAC GAG ACC AAG TGC AAT CCC ATG GGT
 V   S   K   Q   L   K   Q   Y   K   M   T   Y   E   T   K   C   N   P   M   G

TAC ACA GAA GAA TGC AGG GGC ATA GAC CTT ACC ATG GAT AGC CAT TGG AAC TCC CAG TGC CGA
 Y   T   E   E   C   R   G   I   D   L   T   M   D   S   H   W   N   S   Q   C   R

ACT ACC CAG TCG TAC TAC AGG CGG GCC GCA ATG TGT GTA ACC AGC AGA AGA AAA ATT GGC TGG
 T   T   Q   S   Y   Y   R   R   A   A   M   C   V   T   S   R   R   K   I   G   W

CGA TTC ATA AGG GAC ATA TGT TCT TGT ACA TTG ACC ATT AAA AGG AGA
 R   F   I   R   D   I   C   S   C   T   L   T   I   K   R   R

TAG
stop
```

FIGURE 6A

```
bdnf   ATG      CATCCTTTCCTTACTATGGTTATTCATACTTTGGTTGCATGAAGGCTGCCCCATGAAAGA
ngf-3  ATGTCCATCTGTTTTATGTGATATTTCTCGCTTATCTCCGTGCATCCAAGGTAACACATGGATCA
ngf    ATGTCCATGTGTTCTACACTCTGATCACACTCTTTCTGATCGGCATACAGGCGGAACCACTCAGA AGCAAACATCCGAGGACAAGGT------GGCTTGGCCTACCCAGGTGTGCGG---ACC------CATGGGACTCT
AAGGAGTTTGCCAGAAGACTCGCTCAATTCCCTCATTATTAAGCTGATCCAGGCAGATATTTGAAAAACAAGCT
GAGCAATGTCCCTGCA---GGA---CAC------ACCATCCCCCAAGTCCACTGGACTAAACTTCAGCATTCCCT GGAGAGC------GTGAATGGGCCCAAGGCAGGTTCAAGAGGCTTGACATCATTGGCTGACACTTTCGAACACGT
CTCCAAGCAGATGGTGGACGTTAAGGAAAATTACCAGAGCACCCTGCCCAAAGCTGAGGCTCCCCGAGAGCCGGA
TGAC------ACTGCC---CTTCGCAGAGCC---CGCAGCGCC---CCG---GCAGCGGCGATAGCTGCACGCGT GATAGAAGAGCTGTTGGATGAGGAC---CAGAAAGTTCGGCCCAATGAAGAAAAC------AATAAGGACGCAGA
GCGGGGAGGGCCCGCCAAGTCAGCATTCCAGCCAGTGATTGCAATGGACACCGAACTGCTGCGACAACAGAGACG
GGCGGGG---CAGACCCGC---AACATT---ACTGTG-------GACCCCAGGCTGTTT---AAAAAGCGGCG CTTGTACACGTCCAGGGTGATGCTCAGTAGTAGTCAAGTGCCTTTGGAGCCTCCTCCTCTTCTCTTTCTGCTGGAGGAATA
CTACAACTCACCGCGGTCCTGCTGAGCGACAGCAGCACCCCCTTGGAGCGCCCCTTGTATCTCATGGAGGATTA
ACTCCGTTCACCCGTGGTGCTGTCTGTTTAGCACCCAGCCTGAAGCTGCAGACACTCAGGATCTGGACTTCGA CAAAAATTACCTAGATGCTGCAAACATGTCCAATGAGGGTCCGGCGC------CACTCTGACCCTGCCCGCCGAGG
CGTGGGCAGCCCCGTGGTGGCGAACAGAACATCACGGCGGAAACGG---TACGCGGAGCATAAGAGTCACCGAGG
GGTCGGTGGTGCTGCCCCCTTCAACAGGACTCAGGAGCAAGCGGTCATCATCCCATCCTTCCACAGGG GGAGCTGAGCGTGTGTGACAGTATTAGTGAGTGGGTAACGCGGCAGCAAAAAGACTGCAGTGGACATGTCGGG
GGAGTACTCGGTATGTGACAGTGAGAGTCTGTGGGTGACC------GACAAGTCATCGGCCATCGACATTCGGGG
CGAATTCTCGGTGTGTGTGACAGTGTCAGCGCGTGTGGGTTGGG------GATAAGACCACCGCCACAGACATCAAGG
```

FIGURE 6B

```
CGGGACGGTCACAGTCCTTGAAAAGGTCCCTGTATCAAAAGGCCAACTGAAGCAATACTTCTACGAGACCAAGTG
ACACCAGTCACGGTGCTGGGGAGATCAAAACGGGCAACTCTCCCGTCAAACAATATTTTATGAAACGCGATG
CAAGGAGGTGATGGTGGTGTTGGGAGAGGTGAACATTAACAACAGTGTATTCAAACAGTACTTTTTGAGACCAAGTG
CAATCCCCATGGGTTACACAAAAGAAGGCTGCAGGGGCATAGAGACAAAAGGCATTGGAACTCCCAGTGCCGAACTAC
TAAGGAAGCCAGGCCGGTCAAAAACGGTTGCAGGGGTATTGATGATAAACACTGAACTCTCAGTGCAAAACATC
CCGGGACCCAAATCCCGTTGACAGCGGGTGCCGGGGCATTGACTGAACTGAACCACTGAACTCATATTGTACCACGAC

CCAGTCGTACGTGCGGGCCCTTACCATGGATAGCAGAAAGAGAATTGGCTGGCGATTCATAAGGATAGACACTTC
CCAAACCTACGTCCGAGCACTGACTTCAGAGAACAATAAACTCGTGGGCTGGGATACGGATAGACACGTC
TCACACCTTTGTCAAGGCGCTGACCATGGAT- - AAGCAGGCTGCCTGGCGGTTTATCCGGATAGATACGGC

TTGTGTATGTACATTGACCATTAAAAGGGGAAGATAG          bdnf
CTGTGTGTGTGCCTTGTCGAGAAAAATCGGAAGAACATGA      ngf-3
CTGTGTGTGTGTGCTCAGTGCAGGAAGGCTGTGAGAAGAGCCTGA  ngf
```

FIGURE 7

```
bdnf  MTILFLHIMVISYFGCMKAAPMKEANIRGQG-GLL
ngf-3 MSILFYLHILFYVILFLAYLRGIQGNNMDQRSLPEDSLNSL
ngf   MSMLFYTLITAFLIGIQAEPHSESNVPA-G-H-

AYPGVRT--HGTLES--VNGPKAGSRGLTSLADTFEH
      HIKLIQADILKNKLSKQ--QMVDSKQ-TA-LKNKLSKQ
      TIPQVHWTKLQHSLD--TA-

VIEELDED-QKVRPNEENKDADLYTSRVMLSSQV
      ERGGPAKSAFQPVIAMDTELLRQQKRRYNSPRVLLSDST
      VAG-QTR-NI-TDPRLF-KKRRLRSPRVLFSTQP

PLEPPLFLLEEYKNYLDAANMSMRVRRHSDPARRGG
      PLEPPLYLMEDYVGSPVVANRTSRRKRAEHKSHRG
      PREADTQDLDFEGGAAPFNRTHRS-YAEHKSHRG

ELSVCDSIEWVTAADKKTKSSAIHTVTIVLEKVPVSKN
      EYSVCDSLYETIKCNPMGYTKEGCRGIDSATDIHVLEEIKTGN
      EFSVCDSVFETIKCRDPKTVPDSGCRGIDKRRSSHPIFIRTGN

QLKQYFYETHKCRRRKIDGHHQRKVEETVLGENSQCYQCTH
      SPVKQYFFEFTKCNDKEVMVYGHHIDRKVGEEVNRCQQTS
      SVFKQYFFETIKCRKVYTLVSSKHWNHWNSYCTT

SYVRALTMDSENNKLQAARIDTSCVCVLSRGKIRR
      TYYALTMDG--KQAAAVTHTDTACVCVLSRKAVRR
      TFVKALTM KLTA.
```

PRODUCTION OF BIOLOGICALLY ACTIVE NGF PROTEINS

CROSS-REFERENCE TO RELATED APPLICATIONS

This is a continuation of Ser. No. 08/087,912 filed on Jul. 6, 1993, now abandoned which is a continuation of application Ser. No. 08/087,912 filed on Jul. 6, 1993, now abandoned, which is a continuation of Ser. No. 07/680,681 filed on Apr. 4, 1991, now abandoned, which is a continuation-in-part of U.S. applications Ser. No. 07/594,126 filed Oct. 9, 1990 now U.S. Pat. No. 5,235,043, Ser. No. 07/547,750 filed Jul. 2, 1990, now abandoned and Ser. No. 07/505,441 filed Apr. 6, 1990, now abandoned, for "Production of Biologically Active, Recombinant Members of the NGF/BDNF family of Neurotrophic Proteins."

FIELD OF INVENTION

This invention relates to processes for the production of recombinant members of the human NGF/BDNF family of neurotrophic proteins in biologically active forms. In addition, this invention discloses processes for identifying previously unreported members of this family of proteins and the subsequent production of these proteins.

BACKGROUND OF THE INVENTION

Neurotrophic factors are natural proteins, found in the nervous system or in non-nerve tissues innervated by the nervous system, whose function is to promote the survival and maintain the phenotypic differentiation of nerve and/or glial cells (Varon and Bunge 1978 *Ann. Rev. Neuroscience* 1:327; Thoenen and Edgar 1985 *Science* 229:238). Because of this physiological role, neurotrophic factors may be useful in treating the degeneration of nerve cells and loss of differentiated function that occurs in a variety of neurodegenerative diseases, such as Alzheimer's or Parkinson's diseases, or after traumatic injuries, such as stroke or physical trauma to the spinal cord (Appel 1981 *Ann. Neurology* 10:499).

In order for a particular neurotrophic factor to be potentially useful in treating nerve damage, the class or classes of damaged nerve cells must be responsive to the factor. Different neurotrophic factors typically affect distinctly different classes of nerve cells. Therefore, it is advisable to have on hand a variety of different neurotrophic factors to treat each of the classes of damaged neurons that may occur with different forms of disease or injury.

A given neurotrophic factor, in addition to having the correct neuronal specificity, must be available in sufficient quantity to be used as a pharmaceutical treatment. Also, since neurotrophic factors are proteins, it would be desirable to administer to human patients only the human form of the protein, to avoid an immunological response to a foreign protein.

Since neurotrophic factors are typically present in vanishingly small amounts in tissues (e.g., Hofer and Barde 1988 *Nature* 331:261; Lin et al. 1989 *Science* 246:1023) and since human tissues are not readily available for extraction, it would be inconvenient to prepare pharmaceutical quantities of human neurotrophic factors directly from human tissues. As an alternative, it would be desirable to isolate the human gene for a neurotrophic factor and use that gene as the basis for establishing a recombinant expression system to produce potentially unlimited amounts of the human protein.

Two neurotrophic factors have been described that are closely related in amino acid sequence but which affect different, although partially overlapping, sets of responsive neurons (Leibrock et al. 1989 *Nature* 341:149). These two neurotrophic factors are: (1) nerve growth factor (NGF) and (2) brain-derived neurotrophic factor (BDNF). Both NGF and BDNF are apparently synthesized as larger precursor forms which are then processed, by proteolytic cleavages, to produce the mature neurotrophic factor (Edwards et al, 1986 *Nature* 319:784; Leibrock et al. 1989 ibid.). The only genes for members of the proposed NGF/BDNF family of neurotrophic proteins that have been reported to date are the human and various animal genes for NGF (Scott et al. 1983 *Nature* 302:538; Ullrich et al. 1983 *Nature* 303:821; Meier et al. 1986 *EMBO J.* 5:1489) and the pig gene for BDNF (Leibrock et al. 1989 ibid.). There is a significant similarity in amino acid sequences between mature NGFs and mature BDNF, including the relative position of all six cysteine amino acid residues, which is identical in mature NGFs and BDNF from all species examined (Leibrock et al 1989 ibid.). See FIG. 7, comparing and emphasizing the similarities of human forms of NGF and BDNF. This suggests that the three-dimensional structure of these two proteins, as determined by the location of disulfide bonds, is similar. Both mature proteins also share a basic isoelectric point (pI).

NGF is a neurotrophic factor at least for cholinergic neurons in the basal forebrain (Hefti and Will 1987 *J. Neural Transm.* [*Suppl*] (*AUSTRIA*) 24:309). The functional inactivation and degeneration of the basal forebrain cholinergic neurons responsive to NGF in the course of Alzheimer's disease is thought to be the proximate cause of the cognitive and memory deficits associated with that disease (Hefti and Will 1987 ibid.). NGF has been shown to prevent the degeneration and restore the function of basal forebrain cholinergic neurons in animal models related to Alzheimer's disease, and on this basis has been proposed as a treatment to prevent the degeneration and restore the function of these neurons in Alzheimer's disease (Williams et al. 1986 *Proc. Natl. Acad. Sci. USA* 83:9231; Hefti 1986 *J. Neuroscience* 6:2155; Kromer 1987 *Science* 235:214; Fischer et al. 1987 *Nature* 329:65).

BDNF is a neurotrophic factor for sensory neurons in the peripheral neurons system (Barde 1989 *Neuron* 2:1525). On this basis, BDNF may prove useful for the treatment of the loss of sensation associated with damage to sensory nerve cells that occurs in various peripheral neuropathies (Schaumberg et al., 1983 "Disorders of Peripheral Nerves" F. A. Davis Co., Philadelphia, Pa.).

Recombinant expression systems that are capable of producing the large quantities of fully-biologically-active and structurally-unmodified mature NGF needed for pharmaceutical development are highly desireable. See, European Patent Publication EP 89113709, describing the recombinant expression of NGF in insect cells. Mature, biologically-active, NGF can be produced when human or animal NGF genes are expressed in eukaryotic cell expression systems (e.g., Edwards et al. 1988 *Molec. Cell. Biol.* 8:2456). In such systems, the full-length NGF precursor is first synthesized and then proteolytically processed to produce mature NGF which is correctly folded 3-dimensionally and is fully biologically active. However, eukaryotic cell expression systems often produce relatively low yields of protein per gram of cells and are relatively expensive to use in manufacturing.

In contrast, expression systems that use prokaryotic cells, such as bacteria, generally yield relatively large amounts of expressed protein per gram of cells and are relatively inexpensive to use in manufacturing. However, an adequate bacterial expression system capable of producing fully-biologically-active and structurally-unmodified mature NGF has not been described. A bacterial expression system is disclosed in Canadian Patent No. 1,220,736. However, no procedures for refolding the expressed protein are presented. This failure can probably be traced to problems associated with bacterial expression systems in general and problems associated with the specific techniques employed to produce NGF in bacteria.

Bacteria are not able to correctly process precursor proteins, such as the precursor protein for NGF, by making appropriate proteolytic cleavages in order to produce the correct smaller mature protein. Therefore, to produce mature NGF in bacteria, it is necessary to express only that portion of the NGF DNA sequence encoding the mature protein and not that for the larger precursor form. When this was done in the bacterium *Escherichia coli*, relatively large amounts of the mature human NGF protein were produced (see, e.g., Iwai et al. 1986 *Chem. Pharm. Bull.* 34:4724; Dicou et al. 1989 *J Neurosci. Res.* 22:13; EP application 121,338). Unfortunately, the bacterially-expressed protein had little or no biological activity.

A protocol for refolding bacterially expressed NGF has been described in European Patent Application 336,324 which restores some biological activity to mature NGF produced in bacteria. However, this protocol has serious deficiencies.

Mature human NGF has generally been unavailable in sufficient amounts for pharmaceutical use, since many eukaryotic expression systems are expensive and often do not produce adequate amounts of mature NGF. Bacterial expression systems described so far have not produced biologically-active and chemically-unmodified mature NGF in sufficient quantities for pharmaceutical use. Since human mature NGF is likely to be useful in the treatment of Alzheimer's disease, the unavailability of this material has been keenly felt by the scientific and clinical communities. The unavailability of biologically-active human mature NGF was seen by a panel of leading scientists, assembled by the National Institute on Aging, as the critical block to further development of NGF as a treatment for Alzheimer's disease (Phelps et al. 1989 *Science* 243:11).

It is presumed that similar manufacturing difficulties would apply to each member of the NGF/BDNF family of neurotrophic proteins, since members of this family so far described have identically located cysteine amino acid residues and presumably, therefore, form a pattern of intramolecular disulfide bonds identical to that of NGF (Angeletti et al. 1973 *Biochemistry* 12:100).

In view of the apparent value of such neurotrophic proteins and the current restraints on the production of large quantities of the biologically active proteins as indicated above, it would be desirable to provide the following: (1) the identification, isolation and characterization of all members of the NGF/BDNF family of neurotrophic proteins; i.e., proteins that are structurally related to NGF and BDNF in a manner similar to the way these two proteins are related to each other; (2) the identification, isolation and characterization of all naturally occurring human members of the NGF/BDNF family of neurotrophic proteins, including specifically human BDNF; (3) the isolation and characterization of genes coding for any and all members of the NGF/BDNF family of neurotrophic proteins, including specifically the human genes coding for all such family members; (4) methods for using the human genes to establish recombinant expression systems in microorganisms such as *E. coli* that will produce significant quantities of the mature (processed) form of these human proteins; (5) methods for refolding members of the NGF/BDNF family of neurotrophic proteins to allow them to obtain a biological specific activity; and (6) pharmaceutical compositions for the treatment of neurological diseases comprised of any one or any combination of the members of the NGF/BDNF family of neurotrophic proteins.

SUMMARY OF THE INVENTION

The present invention relates to processes for the production of biologically active members of the NGF/BDNF family of neurotrophic proteins, to the nucleic acid sequence of the gene coding for human BDNF and the inferred amino acid sequence for human BDNF, and to the nucleic acid sequences of genes coding for previously unreported members of this family of neurotrophic proteins including NGF-3 and the inferred amino acid sequences of such proteins.

A process for expressing members of the NGF/BDNF family of neurotrophic proteins in an efficient bacterial expression system, specifically in *Escherichia coli*, is set forth. In addition, a process for restoring biological activity to mature but biologically inactive human neurotrophic proteins produced in bacteria is described.

More specifically, a method for the expression of NGF and the effective renaturing of human mature NGF in a biologically active form is described. A previously undescribed member of the NGF/BDNF family of neurotrophic proteins, designated herein as NGF-3, has been identified, and the nucleic acid sequence of the human gene coding for NGF-3 has been identified and the inferred amino acid sequence of NGF-3 described.

The present invention also includes the production of purified forms of all members of the NGF/BDNF family of neurotrophic proteins which would be valuable as pharmaceutical preparations for treating the degeneration of nerve cells and loss of differentiated function that occurs in a variety of neurodegenerative diseases. This application describes and claims the gene coding for human brain-derived neurotrophic factor (BDNF) comprised substantially of the nucleic acid sequence as is set forth in FIG. 1, and this sequence where A is substituted for G at position 196 and/or at position 668. Also described are mature human brain-derived neurotrophic factor (BDNF) comprised substantially of the amino acid sequence as is set forth in FIG. 1, and this sequence where methionine is substituted for valine at amino acid 66 and/or lysine is substituted for arginine at amino acid 223. Human mature NGF-3 comprised of the amino acid sequence as is set forth in FIG. 7 and the gene coding for human mature NGF-3 comprised of the nucleic acid sequence as is set forth in FIG. 6.

A method for refolding and renaturing neurotrophic proteins wherein the proteins attain substantially full biological activity which comprises creating a reaction medium that allows said neurotrophic protein to assume a variety of 3-dimensional conformations and intramolecular disulfide bonding patterns wherein substantially all of said protein will assume its energetically most stable formation; and isolating said neurotrophic protein from said reaction medium.

A bacterial cell expression system for producing the mature biologically active form of a human neurotrophic protein which comprises: inserting the gene coding for said protein into a vector; expressing said gene to form a biologically inactive form of said protein; and refolding and renaturing said biologically inactive form.

Pharmaceutical compositions for the treatment of neurological diseases in humans comprising biologically active human NGF-3, human BDNF and/or human NGF in an acceptable pharmaceutical carrier.

It is to be understood that both the foregoing general description and the following detailed description are exemplary and explanatory only, and are not restrictive of the invention, as claimed. The accompanying drawings, which are incorporated in and constitute a part of the specification, illustrate various embodiments of the invention and, together with the description, serve to explain the principles of the invention.

BRIEF DESCRIPTION OF THE DRAWINGS

FIG. 1 depicts the nucleic acid and inferred amino acid sequences of human BDNF. The inferred amino acid sequence of the mature (processed) form of BDNF is in bold.

FIG. 6A–B compares the nucleic acid sequence of NGF-3 to the sequence of NGF and BDNF. Gaps, indicated by dashes, correspond to the location of gaps used to align the amino acid sequences (see FIG. 7). The partial nucleic acid sequence of NGF-3 obtained by PCR is underlined.

FIG. 7 compares the amino acid sequence of NGF-3 to the sequence of NGF and BDNF. The inferred sequences of the mature proteins are in bold. Each amino acid underlined in the mature sequence of BDNF or NGF is identical to the corresponding amino acid in NGF-3. Each amino acid underlined in the mature sequence of NGF-3 is identical to the corresponding amino acids in both NGF and BDNF. Gaps, indicated by dashes, were placed in the sequences to increase alignment. The six cysteines found in BDNF, NGF and NGF-3 are found in the same locations in all three proteins, and are bracketed.

DESCRIPTION OF THE PREFERRED EMBODIMENTS

Figure 2:
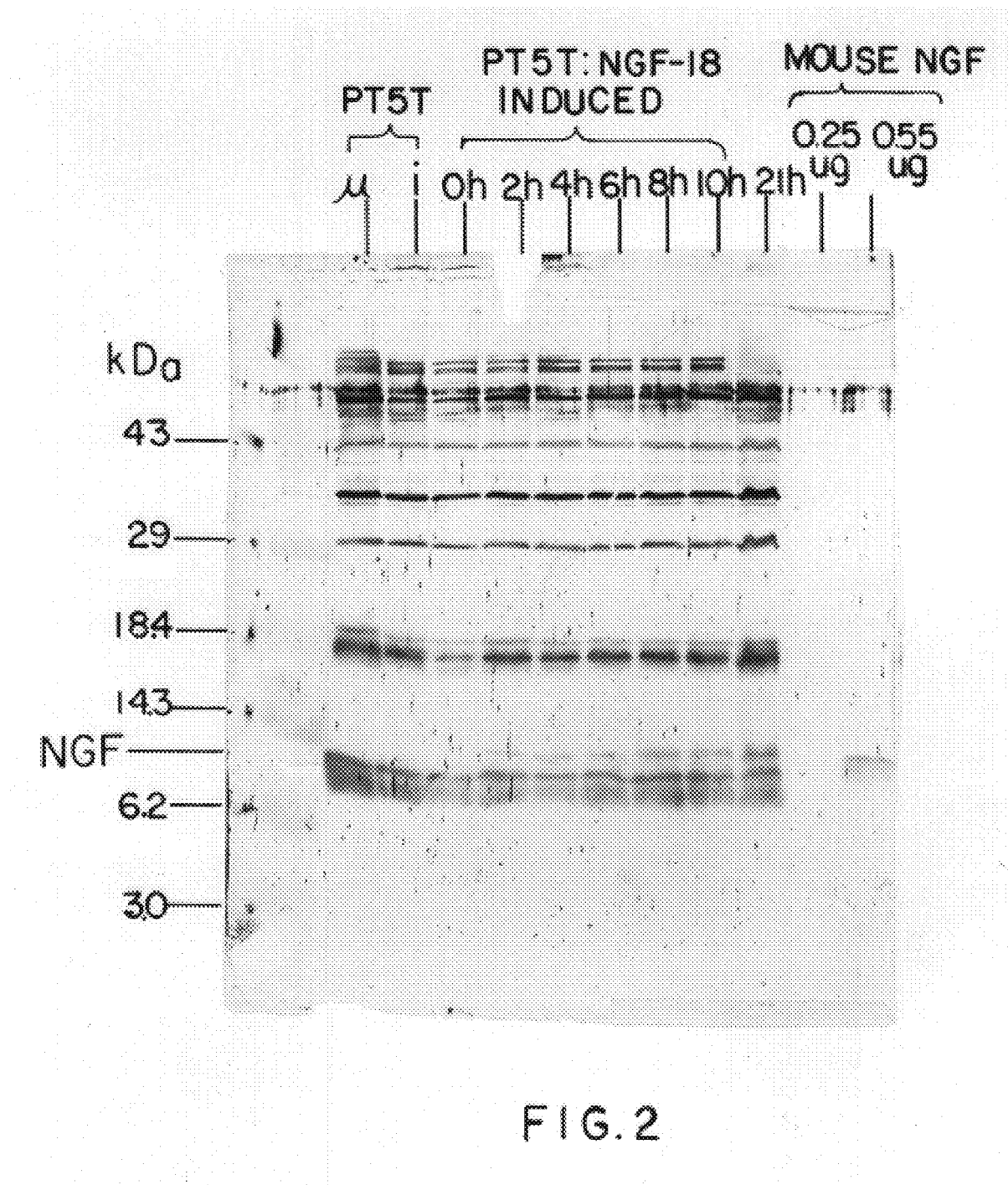
FIG. 2 depicts the expression of human mature (processed) NGF in E. coli in vector pT5T. The details are given in the text of Example 2.

Reference will now be made in detail to the presently preferred embodiments of the invention which, together with the following examples, serve to explain the principles of the invention.

This invention describes many aspects of the identification and production of a "family" of neurotrophic proteins. NGF and BDNF appear to define a family of structurally related neurotrophic proteins which are likely to differ in their physiological role in the organism, each member affecting a different set of responsive neurons. It would be highly desirable to isolate the genes for any and all additional members of this NGF/BDNF family, in order to have a battery of neurotrophic proteins available to treat the range of different nerve cell types whose functions are compromised in various forms of damage to the nervous system.

It is desireable to utilize human proteins for treating humans. In accordance with this principle it would be desirable to obtain the human gene for BDNF in order to manufacture the human protein. Also in accordance with this principle and with the principle expressed above that it would be desirable to have a battery of neurotrophic proteins with differing neuronal specificities to treat a variety of neurological conditions, it would be desirable to obtain the human genes for any and all additional members of the NGF/BDNF family of neurotrophic proteins.

The inability to obtain biologically active bacterially expressed NGF has been a major hurdle in this field. The likely reason for this lack of biological activity is that the mature NGF protein was unable to assume spontaneously the correct 3-dimensional structure and form the correct intramolecular disulfide bonds, both of which are essential for biological activity. Therefore, it would appear necessary to develop a refolding protocol capable of restoring to the mature NGF produced in bacteria the 3-dimensional structure and intramolecular disulfide bonding pattern required for full biological activity.

The protocol for refolding NGF described in European Patent Applications 336,324 does not adequately solve the problem. The protocol uses exposure to high pH (pH 13 is recommended)—apparently to break disulfide bonds that may have formed incorrectly in the bacterially-produced NGF—followed by lowering of the pH—apparently to allow the opportunity for the correct intramolecular disulfide bonds to form. Exposure to high pH, as used in this protocol, is known to cause extensive modification of proteins, including the elimination of amine side chains in glutamine and asparagine (of which there are 7 in mature human NGF) and extensive chemical alteration of asparagine-glycine, asparagine-serine and asparagine-threonine adjacent pairs (of which there are 2 in mature human NGF). In addition to these chemical modifications, the refolding procedure appeared to restore only approximately one-tenth of the biological activity of NGF. The protocol described in European Patent application 336,324 would, therefore, appear to be inadequate to produce fully-biologically-active and chemically-unmodified mature human NGF. Although numerous protocols for refolding and renaturing proteins that do not involve harsh conditions exist, no such procedure has been applied successfully to NGF. For a general review of refolding procedures see, H. Kohno, *Methods Enzymol.*, vol. 185, pg. 187 (1990).

Based on these considerations, a manufacturing system capable of producing fully-biologically-active and chemically-unmodified human mature NGF in large amounts in bacteria will be useful in producing similar large amounts of any member of the NGF/BDNF family in a biologically-active and unmodified form suitable for pharmaceutical use.

1. Isolation of Human BDNF

In one embodiment of the present invention methods are provided for obtaining the human gene coding for the precursor and mature forms of BDNF. The present invention includes the mature and precursor forms of human BDNF, and the genes that code for such proteins. Throughout this application, the mature form of a neurotrophic protein refers to the biologically active form of the protein as it exists in nature after proteolytic cleavage. The precursor form of a neurotrophic protein refers to the protein coded for by the human gene prior to proteolytic cleavage. In a preferred version of this embodiment, and as described in Example 1 below, synthetic oligonucleotides BDNF-1, BDNF-2, BDNF-2A, BDNF-2B, BDNF-3, BDNF-4 and BDNF-5, approximately 15–30 bases in length, were prepared based on various regions of the nucleic acid sequence encoding pig BDNF. These pig BDNF oligonucleotides are used in various combinations as primers in the polymerase chain reaction (PCR) with human genomic DNA as template to amplify intervening segments of the human gene for BDNF. The amplified fragments are subcloned and the subclones screened for those that hybridize to an additional oligonucleotide probe representing sequences located between those of the two primers used in PCR.

Positive subclones isolated in this screening may be sequenced to confirm their identity as portions of the BDNF gene. One or more of these amplified fragments may be used to screen a human genomic DNA library in order to obtain the human gene for BDNF. Subcloned restriction fragments of human genomic clones may be sequenced in order to provide the nucleic acid and inferred amino acid sequences coding for the precursor and mature forms of human BDNF. The nucleic acid and inferred amino acid sequences of human BDNF, obtained according to these procedures and included within the scope of this invention, are set forth in FIG. 1.

2. Identification of Previously Undescribed Members of the NGF/BDNF Family of Neurotrophic Proteins In one embodiment of the present invention methods are provided for obtaining the human genes coding for the precursor and mature forms of previously-unreported, new members of the NGF/BDNF family of neurotrophic proteins. The desired human DNA sequences are any and all previously-unreported sequences that code for proteins which are not identical to human NGF or BDNF but are clearly related to NGF or BDNF with respect to possible defining characteristics of the family. Such characteristics may include one or more of the following: neurotrophic activity in an appropriate bioassay; significant homology in amino acid sequence including both amino acid identities and conservative substitutions; conserved location of cysteine residues in the amino acid sequence; hydrophobic signal sequences for secretion of the protein; signal sequences for proteolytic processing to a mature form; and/or basic isoelectric point of the processed protein.

A. In one preferred version of this embodiment, several synthetic oligonucleotide, approximately 15–40 bases in length, may be prepared based on a number of both conserved and variable regions of the nucleic acid sequences encoding animal and human NGFs and BDNFs. These NGF/BDNF oligonucleotide may be used in various combinations as primers in PCR with human genomic DNA or human cDNA libraries prepared from a variety of discrete regions of the nervous system as templates in order to amplify intervening segments of the human genes for members of the NGF/BDNF family.

Using cDNAs from discrete regions of the nervous system may be advantageous since (1) regions that do not contain significant amounts of the messages for NGF and BDNF may reduce the background of fragments amplified by PCR from NGF and BDNF themselves; and, (2) neurotrophic factors that affect desired neuronal populations are likely to be located in predictable regions of the nervous system.

The amplified fragments may be subcloned and individual subclones selected for sequencing either (a) by positive hybridization to a degenerate oligonucleotide representing DNA sequences located between those of the oligonucleotide primers, or (b) by restriction mapping to detect subclones containing an insert of approximately the size one would expect to be amplified from NGF or BDNF.

Such selected subclones may be sequenced to determine whether they represent portions of the gene for NGF, BDNF, or new members of the NGF/BDNF family. If the subcloned, amplified fragment appears to represent a new member of the NGF/BDNF family, this fragment may be radiolabeled and used to screen a human genomic DNA library in order to obtain the human gene for the putative new neurotrophic protein. The human gene may be sequenced in order to provide the nucleic acid and inferred amino acid sequences coding for the precursor and mature forms of the new neurotrophic protein.

B. In a second preferred version of this embodiment, subdlones of the fragments amplified by PCR as described above, may be screened with each of several non-degenerate DNA fragments that are specific for the NGF or BDNF genes. The purpose of this screening is to facilitate isolation of fragments amplified from genes for new members of the NGF/BDNF family, by eliminating fragments amplified from the already characterized members NGF and BDNF. Amplified fragments that have been identified in this way as being different from NGF and BDNF may be sequenced to confirm their identity and, if appropriate, used to obtain the human gene, as described above.

C. In a third preferred version of this embodiment, a human genomic library and human cDNA libraries prepared from a variety of discrete regions of the nervous system may be screened to locate clones containing possible new members of the NGF/BDNF family. Such libraries may be screened either with a portion of the human DNA sequences encoding NGF or BDNF or with one of several synthetic oligonucleotide, approximately 15–40 bases in length, prepared based on various conserved and variable regions of the nucleic acid sequences encoding animal and human NGFs and BDNFs. Reducing the stringency of hybridization during screening of these libraries allows the probes to hybridize not only to clones containing NGF and BDNF sequences but also to clones containing similar, and possibly related, sequences. Screening cDNA libraries from regions of the nervous system that do not contain significant amounts of the messages for NGF and BDNF may be advisable in order to reduce the background of NGF and BDNF clones. Clones identified in these screens may either be sequenced to determine whether they represent the genes for new members of the NGF/BDNF family or they may be further screened, as described in the preceding paragraph, to eliminate those which are likely to represent the genes for the already known members, NGF and BDNF.

Each of the three preferred versions of this embodiment can be used to provide the nucleic acid and inferred amino acid sequences encoding the precursor and mature forms of new human members of the NGF/BDNF family of neurotrophic proteins. This invention encompasses any and all previously-unreported members of the NGF/BDNF family of neurotrophic proteins.

A new member of the NGF/BDNF family of neurotrophic proteins has been identified utilizing the procedures set forth above. As described in Example 4 below and seen in FIG. 6, the complete nucleic acid sequence has been identified that encodes the previously unreported protein NGF-3. Based on the nucleic acid sequence as set forth in FIG. 6 the complete inferred amino acid sequence of mature and precursor NGF-3 has been obtained. The amino acid sequence of NGF-3, inferred by reference to the sequenced NGF-3 gene, is set forth in FIG. 7.

In addition, the invention encompasses neurotrophic proteins of any origin which are biologically equivalent to the neurotrophic proteins described herein. In the preferred embodiment, this invention encompasses mature human neurotrophic proteins. Throughout this specification, any reference to a neurotrophic protein should be construed to refer to the proteins identified and described herein as members of the NGF/BDNF family of neurotrophic proteins.

By "biologically equivalent" as used throughout the specification and claims, we mean compositions of the present invention which are capable of promoting the survival and maintaining the phenotypic differentiation of nerve or glial cells, but not necessarily to the same degree as the native neurotrophic proteins described herein. By "substantially homologous" as used throughout the ensuing specification and claims, is meant a degree of homology to the native neurotrophic proteins in excess of that displayed by any previously reported neurotrophic proteins. Preferably, the degree of homology is in excess of 70%, most preferably in excess of 80%, and even more preferably in excess of 90%, 95% or 99%. A particularly preferred group of neurotrophic proteins are in excess of 95% homologous with the native proteins. The percentage of homology as described herein is calculated as the percentage of amino acid residues found in the smaller of the two sequences which align with identical amino acid residues in the sequence being compared when four gaps in a length of 100 amino acids may be introduced to assist in that alignment as set forth by Dayhoff, in *Atlas of Protein Sequence and Structure* Vol. 5, p. 124 (1972), National Biochemical Research Foundation, Washington, D.C., specifically incorporated herein by reference. Also included as substantially homologous are those neurotrophic proteins which may be isolated by virtue of cross-reactivity with antibodies to the described protein or whose genes may be isolated through hybridization with the gene or with segments of the described protein.

3. Gene Expression

In one embodiment of the present invention, each of the human genes for members of the NGF/BDNF family of neurotrophic proteins, including the human genes for NGF, BDNF and NGF-3 may be used to establish recombinant expression systems for manufacture of the mature human neurotrophic protein encoded by each gene. In a preferred version of this embodiment, expression may occur in a microorganism, in particular *Escherichia coli*.

The gene for each neurotrophic protein may be modified to facilitate efficient expression in *E. coli*. Such modifications, described in more detail below, may include, but are not limited to, the following: (i) preparation of a DNA sequence that encodes only the inferred mature (processed) form of the protein, by removal of additional coding and non-coding sequences that may be present in the gene; (ii) alteration of human codons to those used preferentially by *E. coli*; (iii) addition of a translational coupler to promote efficient translation in *E. coli*; (iv) insertion of new restriction sites for convenience of subsequent ligation and cloning; and (v) insertion of the DNA into one or more of several expression vectors designed to promote efficient expression of the DNA in *E. coli*. The final expression constructs may be transformed into a suitable strain of *E. coli* and transformants producing mature neurotrophic protein selected for scale-up and manufacture. The expression of NGF in *E. coli*, according to a preferred embodiment of this invention, is described in Example 2 below.

A. General

A natural or synthetic DNA sequence may be used to direct production of such neurotrophic proteins. In one embodiment of the invention, alternate forms of the neurotrophic factors may be produced in which the active site functions in a manner biologically equivalent to that of the neurotrophic proteins described herein. The general expression method comprises:

1. preparation of a DNA sequence capable of directing a host cell to produce a protein having neurotrophic activities or a precursor thereof;

2. cloning the DNA sequence into a vector capable of being transferred into and replicated in a host cell, such vector containing operational elements needed to express the DNA sequence or a precursor thereof;

3. transferring the vector containing the synthetic DNA sequence and operational elements into a host cell capable of expressing the DNA encoding the neurotrophic protein or a precursor thereof;

4. culturing the host cells under the conditions for amplification of the vector and expression of the protein or a precursor thereof;

5. harvesting the protein or a precursor thereof; and 6. permitting the protein to assume an active tertiary structure whereby it possesses or can be processed into a protein having biological activity.

B. DNA sequences

DNA sequences contemplated for use in this method are discussed in part in Examples 1, 2 and 4. FIG. 6 sets forth the complete nucleic acid sequences coding for human NGF, BDNF, and NGF-3. It is contemplated that these sequences include synthetic and natural DNA sequences and combinations thereof. The natural sequences further include cDNA or genomic DNA segments.

The means for synthetic creation of polynucleotide sequences encoding a protein identical to that encoded by the cDNA or genomic polynucleotide sequences are generally known to one of ordinary skill in the art, particularly in light of the teachings contained herein. As an example of the current state of the art relating to polynucleotide synthesis, one is directed to Matteucci, M. D., and Caruthers, M. H., in J. Am. Chem. Soc. 103:3185 (1981) and Beaucage, S. L. and Caruthers, M. H. in Tetrahedron Lett. 22:1859 (1981), and to the instructions supplied with an ABI oligonucleotide synthesizer, each of which is specifically incorporated herein by reference.

These synthetic sequences may be identical to the natural sequences described in more detail below or they may contain different nucleotides. In one embodiment, if the synthetic sequences contain nucleotides different from those found in the natural DNA sequences of this invention, it is contemplated that these different sequences will still encode a polypeptide which has the same primary structure as the neurotrophic proteins described herein. In an alternate embodiment, the synthetic sequence containing different nucleotides will encode a polypeptide which has the same biological activity as the neurotrophic proteins described herein.

Additionally, the DNA sequence may be a fragment of a natural sequence, i.e., a fragment of a polynucleotide which occurred in nature and which has been isolated and purified for the first time by the present inventors. In one embodiment, the DNA sequence is a restriction fragment isolated from a cDNA library.

In an alternative embodiment, the DNA sequence is isolated from a human genomic library. An example of such a library useful in this embodiment is set forth by Wyman, et al., (1985) Proc. Nat. Acad. Sci. USA, 82, 2880–2884.

DNA sequences coding for the desired neurotrophic proteins may be obtained in several different methods. Human cDNA libraries and human genomic libraries may be probed with at least one probe capable of binding to the neurotrophic protein gene or its gene product. After identification of genes coding for the protein by virtue of its ability to bind to the probe, the gene may be isolated and linked to operational elements necessary to maintain and express the gene in a host cell.

Another method for identifying and isolating gene sequences is by use of the polymerase chain reaction. As described in Example 1, the natural DNA sequence coding for human BDNF was identified and isolated by preparing several synthetic oligonucleotides designed by review of the nucleic acid sequence for pig BDNF and utilizing pairs of these primers in the polymerase chain reaction to identify amplified fragments of the human BDNF sequence. The amplified fragments obtained by PCR were then used to clone the complete nucleic acid sequence of human BDNF.

As described in Example 4, the natural DNA sequence coding for human NGF-3 was identified and isolated by preparing synthetic oligonucleotides designed by review of the nucleic acid sequence of human and animal NGF and BDNF and utilizing these primers in the polymerase chain reaction to identify an amplified fragment of the previously unreported human NGF-3 sequence. The amplified fragment obtained by PCR was used to clone the complete nucleic acid sequence of human NGF-3.

A DNA sequence, isolated according to these methods from a human genomic DNA library and encoding at least a portion of the human BDNF protein described herein has been inserted into the plasmid pSYN 23. This plasmid has been deposited at the American Type Culture Collection, Rockville, Md., under Accession No. 40992 on Mar. 20, 1992, in accordance with the Budapest Treaty. This DNA sequence is further described in Example 1 below.

C. Vectors (i). Microorganisms, especially *E. coli*

The vectors contemplated for use in the present invention include any vectors into which a DNA sequence as discussed above can be inserted, along with any preferred or required operational elements, and which vector can then be subsequently transferred into a host cell and replicated in such cell. In particular, it is preferred that all of these vectors have some or all of the following characteristics: (1) possess a minimal number of host-organism sequences; (2) be stably maintained and propagated in the desired host; (3) be capable of being present in a high copy number in the desired host; (4) possess a regulatable promoter positioned so as to promote transcription of the gene of interest; (5) have at least one marker DNA sequence coding for a selectable trait present on a portion of the plasmid separate from that where the DNA sequence will be inserted; and (6) a DNA sequence capable of terminating transcription.

The cloning vectors of the present invention contain various operational elements. These "operational elements" include the following: regulators, promoters, transcription terminator, non-translated sequence, ribosome binding sites, leader sequence and translational coupler, translation terminator, selectable marker. In practice, it is possible to construct these vectors in a way that allows them to be easily isolated, assembled and interchanged.

The operational elements as discussed herein are routinely selected by those of ordinary skill in the art in light of prior literature and the teachings contained herein. General examples of these operational elements are set forth in B. Lewin, *Genes*, Wiley & Sons, New York (1983), which is specifically incorporated herein by reference. Various examples of suitable operational elements may be found on the vectors discussed above and may be elucidated through review of the publications discussing the basic characteristics of the aforementioned vectors.

Upon synthesis and isolation of all necessary and desired component parts of the above-discussed vector, the vector is assembled by methods generally known to those of ordinary skill in the art. Assembly of such vectors is believed to be within the duties and tasks performed by those with ordinary skill in the art and, as such, is capable of being performed without undue experimentation. For example, similar DNA sequences have been ligated into appropriate cloning vectors, as set forth by Maniatis et al. in Molecular Cloning, Cold Spring Harbor Laboratories (1984), which is specifically incorporated herein by reference.

Figure 4:
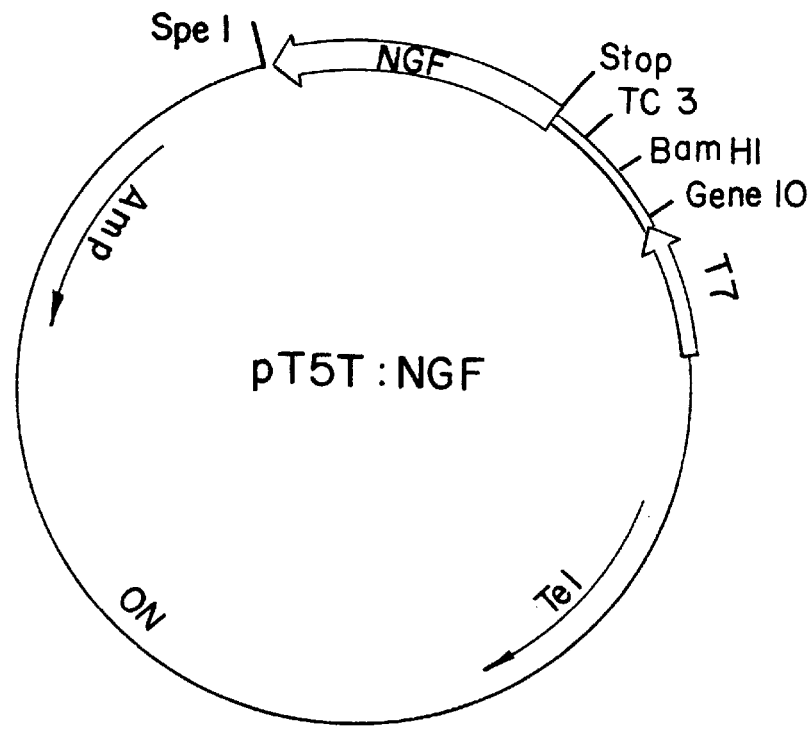
FIG. 4 depicts certain features of the bacterial expression vector pT5T. Features are representative only and not drawn to exact scale. The NGF insert is intended to represent any member of the NGF/BDNF family of neurotrophic proteins.
Figure 5:
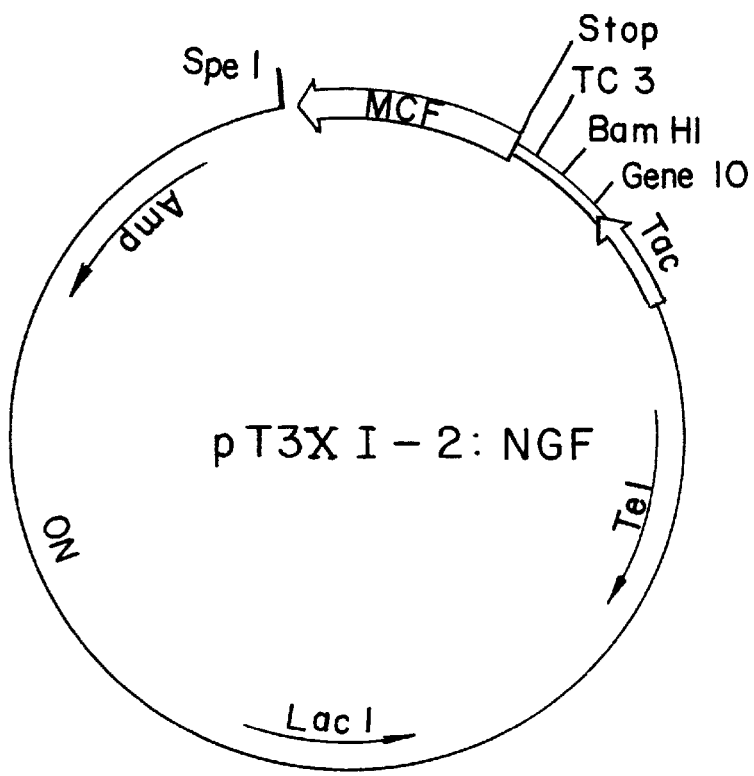
FIG. 5 depicts certain features of the bacterial expression vector pT3XI-2. Features are representative only and not drawn to exact scale. The NGF insert is intended to represent any member of the NGF/BDNF family of neurotrophic proteins.

In Example 2 below, the preparation of two vectors containing the nucleic acid sequence coding for mature human NGF is described. The vectors into which the appropriate nucleic acid sequences were inserted are *E. Coli* expression vectors referred to as pT5T and pT3XI-2. Details of the vector pT5T:NGF are shown in FIG. 4 and details of the vector pT3XI-2:NGF are shown in FIG. 5.

In construction of the cloning vectors of the present invention, it should additionally be noted that multiple copies of the DNA sequence and its attendant operational elements may be inserted into each vector. In such an embodiment, the host organism would produce greater amounts per vector of the desired neurotrophic protein. The number of multiple copies of the DNA sequence which may be inserted into the vector is limited only by the ability of the resultant vector, due to its size, to be transferred into and replicated and transcribed in an appropriate host cell.

(ii) Other Microorganisms

Vectors suitable for use in microorganisms other than *E. coli* are also contemplated for this invention. Such vectors are described in Table 1. In addition, certain preferred vectors are discussed below. These microorganism vectors as described herein are routinely employed by those of ordinary skill in the art in light of prior literature and the teachings contained herein. Assembly of such vectors is believed to be within the duties and tasks performed by those with ordinary skill in the art and, as such, is capable of being performed without undue experimentation.

TABLE 1

| HOSTS | REGULATED PROMOTERS | INDUCER | TRANSCRIPTION TERMINATOR | TRANSCRIPTIONAL STABILIZATION | MRNA | START SITE & LEADER PEPTIDE | RS MARKER | BINDING SITE |
|---|---|---|---|---|---|---|---|---|
| *E. coli* | Lac[1], Tac[2] Lambda pL Trp[5] | IPTG temperature IAA addition or tryptophan depletion | rrnB[6] increased | ompA[8] | bla[11] rrnC[7] trp[10] | ampicillin[14] Lambda int[9] phoS | ompA[12] chloramphenical[16] | tetracycline[14,15] |
| Bacillus | *alpha | *E. coli* rrn amylase[17] *substilisin[18] *p-43[19] spac-I[26] IPTG | rrn BT.T[20] | B. amy neutral B.amy alpha-amylase[22] B.subt. subtilisin[23] | | Kan[r 24] protease[21] | B. amy neural protease Cam[r 25] B. amy alpha-amylase[22] |
| Pseudomonas | Trp[27](*E.coli*) Lac(*E.coli*) Tac(*E.coli*) | IAA addition, or tryptophan depletion IPTG | | | phospholipase C28 exotoxin A[28] | sulfonamide[30] streptomycin[30] | | Trp(*E.coli*) |
| Yeast | Gal 1[31],Glucose 10[32] | Cyc1 depletion and Adb I[33], galactose II[34] Glucose Sac 2 Pho 5 depletion Phosphate depletion | | Invertase[36] Una Alpha factor | Ura 3[37] Acid phosphatase[36] Alpha Factor Tap 1 | Leu 2[38] His 3 | | |

*non-regulated

1. Backman, K., Ptashne, M. and Gilbert, W. Proc. Natl. Acad. Sci. USA 73, 4174–4178 (1976).
2. de Boer, H. A., Comstock, L. J., and Vasser, M. Proc. Natl. Acad. Sci. USA 80, 21–25 (1983).
3. Shimatake, H. and Rosenberg, M. Nature 292, 128–132 (1981).
4. Derom, C., Gheysen, D. and Fiers, W. Gene 17, 45–54 (1982).
5. Hallewell, R. A. and Emtage, S. Gene 9, 27–47 (1980).
6. Brosius, J., Dull, T. J., Sleeter, D. D. and Noller, H. F. J. Mol. Biol. 148 107–127 (1981).
7. Normanly, J., Ogden, R. C., Horvath, S. J. and Abelson, J. Nature 321, 213–219 (1986).
8. Belasco, J. G., Nilsson, G., von Gabain, A. and Cohen, S. N. Cell 46, 245–251 (1986).
9. Schmeissner, U., McKenney, K., Rosenberg M. and Court, D. J. Mol. Biol. 176, 39–53 (1984).
10. Mott, J. E., Galloway, J. L. and Platt, T. EMBO J. 4, 1887–1891 (1985).
11. Koshland, D. And Botstein, D. Cell 20, 749–760 (1980).
12. Movva, N. R., Kakamura, K. and Inouye, M. J. Mol. Biol. 143, 317–328 (1980).
13. Surin, B. P., Jans, D. A., Fimmel, A. L., Shaw, D. C., Cox, G. B. and Rosenberg, H. J. Bacteriol. 157, 772–778 (1984).
14. Sutcliffe, J. G. Proc. Natl. Acad. Sci. USA 75, 3737–3741 (1978).
15. Peden, K. W. C. Gene 22, 277–280 (1983).
16. Alton, N. K. and Vapnek, D. Nature 282, 864–869 (1979).
17. Yang, M., Galizzi, A., and Henner, D. Nuc. Acids Res. 11(2), 237–248 (1983).
18. Wong, S. -L., Price C. W., Goldfarb, D. S., and Doi, R. H. Proc. Natl. Acad. Sci. USA 81, 1184–1188 (1984).
19. Wang, P. -Z. and Doi, R. H. J. Biol. Chem. 251, 8619–8625, (1984).
20. Lin, C. -K., Quinn, L. A., Rodriguez, R. L. J. Cell Biochem. Suppl. (9B), p. 198 (1985).
21. Vasantha, N., Thompson, L. D., Rhodes, C., Banner, C., Nagle, J., and Filpula, D. J. Bact. 159(3), 811–819 (1984).
22. Plava, I., Sarvas, M., Lehtovaara, P., Sibazkov, M., and Kaariainen, L. Proc. Natl. Acad. Sci. USA 79, 5582–5586 (1982).
23. Wong. S. -L., Pricee, C. W., Goldfarb, D. S., and Doi, R. H. Proc. Natl. Acad. Sci. USA 81, 1184–1188 (1984).
24. Sullivan, M. A., Yasbin, R. E., Young, F. E. Gene 29, 21–46 (1984).
25. Vasantha, N., Thompson, L. D., Rhodes, C., Banner, C. Nagle, J., and Filula, D. J. Bact. 159(3), 811–819 (1984).
26. Yansura, D. G. and Henner, D. J. PNAS 81, 439–443 (1984).
27. Gray, G. L., McKeown, K. A., Jones, A. J. S., Seeburg, P. H. and Heyneker, H. L. Biotechnology, 161–165 (1984).
28. Lory, S., and Tai, P. C. Gene 22, 95–101 (1983).
29. Liu, P. V. J. Infect. Dis. 130 (suppl), 594–599 (1974).
30. Wood, D. G., Hollinger, M. F., and Tindol, M. B. J. Bact. 145, 1448–1451 (1981).

31. St. John, T. P. and Davis, R. W. J. Mol. Biol. 152, 285–315 (1981).
32. Hopper, J. E., and Rowe, L. B. J. Biol. Chem. 253, 7566–7569 (1978).
33. Denis, C. L., Ferguson, J. and Young, E. T. J. Biol. Chem. 258, 1165–1171 (1983).
34. Lutsdorf, L. and Megnet, R. Archs. Biochem. Biophys. 126, 933–944 (1968).
35. Meyhack, B., Bajwa, N., Rudolph, H. and Hinnen, A. EMBO. J. 6, 675–680 (1982).
36. Watson, M. E. Nucleic Acid Research 12, 5145–5164 (1984).
37. Gerband, C. and Guerineau, M. Curr. Genet. 1, 219–228 (1980).
38. Hinnen, A., Hicks, J. B. and Fink, G. R. Proc. Natl. Acad. Sci. USA 75, 1929–1933 (1978).
39. Jabbar, M. A., Sivasubramanian, N. and Nayak, D. P. Proc. Natl. Acad. Sci. USA 82, 2019–2023 (1985).

(a) Pseudomonas Vectors

Several vector plasmids which autonomously replicate in a broad range of Gram negative bacteria are preferred for use as cloning vehicles in hosts of the genus Pseudomonas. Certain of these are described by Tait, R. C., Close, T. J., Lundquist, R. C., Hagiya, M., Rodriguez, R. L., and Kado, C. I. in Biotechnology, May, 1983, pp. 269–275; Panopoulos, N.J. in *Genetic Engineering in the Plant Sciences*, Praeger Publishers, New York, N.Y., pp. 163–185 (1981); and Sakagucki, K. in Current Topics in Microbiology and Immunology 96:31–45 (1982), each of which is specifically incorporated herein by reference.

One particularly preferred construction would employ the plasmid RSF1010 and derivatives thereof as described by Bagdasarian, M., Bagdasarian, M. M., Coleman, S., and Timmis, K. N. in *Plasmids of Medical, Environmental and Commercial Importance*, Timmis, K. N. and Puhler, A. eds., Elsevier/North Holland Biomedical Press (1979), specifically incorporated herein by reference. The advantages of RSF1010 are that it is a relatively small, high copy number plasmid which is readily transformed into and stably maintained in both *E. coli* and Pseudomonas species. In this system, it would be preferred to use the Tac expression system as described for Escherichia, since it appears that the *E. coli* trp promoter is readily recognized by Pseudomonas RNA polymerase as set forth by Sakagucki, K. in Current Topics in Microbiology and Immunology 96:31–45 (1982) and Gray, G. L., McKeown, K. A., Jones A. J. S., Seeburg, P. H., and Heyneker, H. L. in Biotechnology, Feb. 1984, pp. 161–165, both of which are specifically incorporated herein by reference. Transcriptional activity may be further maximized by requiring the exchange of the promoter with, e.g., an *E. coli* or *P. aeruginosa* trp promoter. Additionally, the lacI gene of *E. coli* would also be included in the plasmid to effect regulation.

Translation may be coupled to translation initiation for any of the Pseudomonas proteins, as well as to initiation sites for any of the highly expressed proteins of the type chosen to cause intracellular expression of the neurotrophic protein.

In those cases where restriction minus strains of a host Pseudomonas species are not available, transformation efficiency with plasmid constructs isolated from *E. coli* are poor. Therefore, passage of the Pseudomonas cloning vector through an r– m+ strain of another species prior to transformation of the desired host, as set forth in Bagdasarian, M., et al., *Plasmids of Medical, Environmental and Commercial Importance*, pp. 411–422, Timmis and Puhler eds., Elsevier/North Holland Biomedical Press (1979), specifically incorporated herein by reference, is desired.

(b) Bacillus Vectors

Furthermore, a preferred expression system in hosts of the genus Bacillus involves using plasmid pUB110 as the cloning vehicle. As in other host vector systems, it is possible in Bacillus to express the neurotrophic proteins of the present invention as either an intracellular or a secreted protein. The present embodiments include both systems. Shuttle vectors that replicate in both Bacillus and *E. coli* are available for constructing and testing various genes as described by Dubnau, D., Gryczan, T., Contente, S., and Shivakumar, A. G. in *Genetic Engineering*, Vol. 2, Setlow and Hollander eds., Plenum Press, New York, N.Y., pp. 115–131 (1980), specifically incorporated herein by reference. For the expression and secretion of the neurotrophic proteins from *B. subtilis*, the signal sequence of alpha-amylase is preferably coupled to the coding region for the protein. For synthesis of intracellular protein, the portable DNA sequence will be translationally coupled to the ribosome binding site of the alpha-amylase leader sequence.

Transcription of either of these constructs is preferably directed by the alpha-amylase promoter or a derivative thereof. This derivative contains the RNA polymerase recognition sequence of the native alpha-amylase promoter but incorporates the lac operator region as well. Similar hybrid promoters constructed from the penicillinase gene promoter and the lac operator have been shown to function in Bacillus hosts in a regulatable fashion as set forth by Yansura, D. G. and Henner in *Genetics and Biotechnology of Bacilii*, Ganesan, A. T. and Hoch, J. A., eds., Academic Press, pp. 249–263 (1984), specifically incorporated by reference. The lacI gene of *E. coli* would also be included in the plasmid to effect regulation.

(c) Colstridium Vectors

One preferred construction for expression in Clostridium is in plasmid pJU12, described by Squires, C. H. et al., in J. Bacteriol. 159:465–471 (1984) and specifically incorporated herein by reference, transformed into *C. perfringens* by the method of Heefner, D. L. et al., as described in J. Bacteriol. 159:460–464 (1984), specifically incorporated herein by reference. Transcription is directed by the promoter of the tetracycline resistance gene. Translation is coupled to the Shine-Dalgarno sequences of this same $tet^r$ gene in a manner strictly analogous to the procedures outlined above for vectors suitable for use in other hosts.

(d) Yeast Vectors

Maintenance of foreign DNA introduced into yeast can be effected in several ways as described by Botstein, D. and Davis, R. W., in *The Molecular Biology of the Yeast Saccharomyces*, Cold Spring Harbor Laboratory, Strathern, Jones and Broach, eds., pp. 607–636 (1982), specifically incorporated herein by reference. One preferred expression system for use with host organisms of the genus Saccharomyces harbors the neurotrophic protein gene on the 2 micron plasmid. The advantages of the 2 micron circle include relatively high copy number and stability when introduced into cir' strains. These vectors preferably incorporate the replication origin and at least one antibiotic resistance marker from pBR322 to allow replication and selection in *E. coli*. In addition, the plasmid will preferably have the two micron sequence and the yeast LEU2 gene to serve the same purposes in LEU2 defective mutants of yeast.

If it is contemplated that the recombinant neurotrophic proteins will ultimately be expressed in yeast, it is preferred that the cloning vector first be transferred into *Escherichia coli*, where the vector would be allowed to replicate and from which the vector would be obtained and purified after amplification. The vector would then be transferred into the yeast for ultimate expression of the protein.

(iii) Mammalian Cells The cDNA for the neurotrophic protein will serve as the gene for expression of the protein in mammalian cells. It should have a sequence that will be efficient at binding ribosomes such as that described by Kozak, in Nucleic Acids Research 15:8125–8132 (1987), specifically incorporated herein by reference, and should have coding capacity for a leader sequence (see section 3(a)(vi)) to direct the mature protein out of the cell in a processed form. The DNA restriction fragment carrying the complete cDNA sequence can be inserted into an expression vector which has a transcriptional promoter and a transcriptional enhancer as described by Guarente, L. in Cell 52:303–305 (1988) and Kadonaga, J. T. et al., in Cell 51:1079–1090 (1987), both of which are specifically incorporated herein by reference. The promoter may be regulatable as in the plasmid pMSG (Pharmacia Cat. No. 27450601) if constitutive expression of the protein is harmful to cell growth. The vector should have a complete polyadenylation signal as described by Ausubel, F. M. et al. in Current Protocols in Molecular Biology, Wiley (1987), specifically incorporated herein by reference, so that the mRNA transcribed from this vector is processed properly. Finally, the vector will have the replication origin and at least one antibiotic resistance marker from pBR322 to allow replication and selection in E. coli.

In order to select a stable cell line that produces the neurotrophic proteins, the expression vector can carry the gene for a selectable marker such as a drug resistance marker or carry a complementary gene for a deficient cell line, such as a dihydrofolate reductase (dhfr) gene for transforming a $dhfr^-$ cell line as described by Ausubel et al., supra. Alternatively, a separate plasmid carrying the selectable marker can be cotransformed along with the expression vector.

D. Host Cells/Transformation

The vector thus obtained is transferred into an appropriate host cell. These host cells may be microorganisms, insect cells or mammalian cells. In the preferred embodiment of this invention the host cells utilized are microorganisms, and more specifically are E. coli cells.

(i) Microorganisms

It is believed that any microorganism having the ability to take up exogenous DNA and express those genes and attendant operational elements may be chosen. After a host organism has been chosen, the vector is transferred into the host organism using methods generally known to those of ordinary skill in the art. Examples of such methods may be found in Advanced Bacterial Genetics by R. W. Davis et al., Cold Spring Harbor Press, Cold Spring Harbor, N.Y., (1980), which is specifically incorporated herein by reference. It is preferred, in one embodiment, that the transformation occur at low temperatures, as temperature regulation is contemplated as a means of regulating gene expression through the use of operational elements as set forth above. In another embodiment, if osmolar regulators have been inserted into the vector, regulation of the salt concentrations during the transformation would be required to insure appropriate control of the foreign genes.

It is preferred that the host microorganism be a facultative anaerobe or an aerobe. Particular hosts which may be preferable for use in this method include yeasts and bacteria. Specific yeasts include those of the genus Saccharomyces, and especially Saccharomyces cerevisiae. Specific bacteria include those of the genera Bacillus, Escherichia, and Pseudomonas, especially Bacillus subtilis and Escherichia coli. Additional host cells are listed in Table I, supra.

(ii) Mammalian Cells

The vector can be introduced into mammalian cells in culture by several techniques such as calcium phosphate: DNA coprecipitation, electroporation, or protoplast fusion. The preferred method is coprecipitation with calcium phosphate as described by Ausubel et al., supra.

Many stable cell types exist that are transformable and capable of transcribing and translating the cDNA sequence, processing the precursor neurotrophic proteins and secreting the mature protein. However, cell types may be variable with regard to glycosylation of secreted proteins and post-translational modification of amino acid residues, if any. Thus, the ideal cell types are those that produce a recombinant neurotrophic protein identical to the natural molecule.

E. Culturing Engineered Cells

The host cells are cultured under conditions appropriate for the expression of the neurotrophic proteins. These conditions are generally specific for the host cell, and are readily determined by one of ordinary skill in the art in light of the published literature regarding the growth conditions for such cells and the teachings contained herein. For example, Bergey's Manual of Determinative Bacteriology, 8th Ed., Williams & Wilkins Company, Baltimore, Md., which is specifically incorporated herein by reference, contains information on conditions for culturing bacteria. Similar information on culturing yeast and mammalian cells may be obtained from Pollack, R. Mammalian Cell Culture, Cold Spring Harbor Laboratories (1975), specifically incorporated herein by reference.

Any conditions necessary for the regulation of the expression of the DNA sequence, dependent upon any operational elements inserted into or present in the vector, would be in effect at the transformation and culturing stages. In one embodiment, cells are grown to a high density in the presence of appropriate regulatory conditions which inhibit the expression of the DNA sequence. When optimal cell density is approached, the environmental conditions are altered to those appropriate for expression of the DNA sequence. It is thus contemplated that the production of the neurotrophic proteins will occur in a time span subsequent to the growth of the host cells to near optimal density, and that the resultant protein will be harvested at some time after the regulatory conditions necessary for its expression were induced.

4. Renaturing of Expressed Recombinant Proteins

In a preferred embodiment of the present invention, the recombinant mature neurotrophic proteins are purified subsequent to harvesting and prior to assumption of their active structure. This embodiment is preferred as the inventors believe that recovery of a high yield of re-folded protein is facilitated if the protein is first purified. However, in one preferred, alternate embodiment, the neurotrophic protein may be allowed to refold to assume its active structure prior to purification. In yet another preferred, alternate embodiment, the protein is present in its re-folded, active state upon recovery from the culturing medium.

In certain circumstances, the mature neurotrophic protein will assume its proper, active structure upon expression in the host microorganism and transport of the protein through the cell wall or membrane or into the periplasmic space. This will generally occur if DNA coding for an appropriate leader sequence has been linked to the DNA coding for the recombinant protein.

In one embodiment of the present invention, the protein produced in microorganisms may lack substantial biological activity and will need to be refolded and renatured to provide a neurotrophic protein with a biological specific activity expected of members of the NGF/BDNF family. The expected specific activity is either that observed for the protein expressed in eukaryotic cells or that observed for the same or a related protein purified from natural sources (e.g., mouse submaxillary gland NGF and pig brain BDNF).

Often the lack of biological activity in proteins expressed in microorganisms is related to improper formation of intramolecular disulfide bonds. In a preferred version of this embodiment, the recombinant neurotrophic protein produced in *E. coli* may be refolded and renatured to attain the correct configuration of intramolecular disulfide bonds and the expected biological specific activity.

In a preferred version, the recombinant protein may be refolded and renatured by using the following steps:

(1) Any intramolecular or intermolecular disulfide bonds and/or any noncovalent interactions which have occurred involving the mature neurotrophic protein produced in a microorganism are first disrupted. In order to do this, the protein is exposed to sufficient denaturant (for example, guanidine hydrochloride or urea) and sufficient reducing agent (for example, beta-mercaptoethanol, dithiothreitol, or cysteine) to denature the protein, disrupt noncovalent interactions, and reduce disulfide bonds.

(2) After the mature neurotrophic protein has been denatured and reduced, the free thiols present in the reduced protein are oxidized by addition of a large excess of disulfide-containing reagent (for example, glutathione or cystine). This reaction produces mixed disulfide bonds in which each cysteine residue in the mature neurotrophic protein forms a disulfide bond with the monomeric form of the oxidizing agent. This step helps to prevent the formation of incorrect intramolecular disulfide bonds in the neurotrophic protein during subsequent processing.

(3) The denaturant and oxidizing agent are then diluted to a defined concentration and a thiol-containing reagent (for example, cysteine) is added to catalyze disulfide interchange. The objective is to produce an environment in which the denaturant concentration is sufficiently reduced to allow the neurotrophic protein to assume various 3-dimensional configurations and in which the oxidization/reduction potential is adjusted to allow the formation and breaking of disulfide bonds. It is presumed that the proper 3-dimensional structure and disulfide bonding pattern of the mature neurotrophic protein is energetically more stable than other possible conformations. Therefore, conditions in which the neurotrophic protein is allowed to assume a variety of 3-dimensional conformations and intramolecular disulfide bond patterns, will allow a significant proportion of the neurotrophic protein to reform the correct intramolecular disulfide bonding pattern, the correct 3-dimensional structure, and, therefore, to become biologically active.

In a preferred embodiment, recombinant neurotrophic protein is dissolved to a concentration of between 0.1–2 mg/ml in a buffer solution containing urea. If necessary, the pH of such solution is made alkaline by the addition of a higher pH buffer solution, also containing urea, in order to promote disulfide exchange. Reducing agent is added to a final concentration of about 1–15 mM. Oxidation agent is then added to a final concentration of about 15–50 mM. Dilution of the neurotrophic protein containing solution is to about 5–20 fold, and the thiol-containing reagent is added to a concentration such that the solution will contain about 2–3 fold more thiol-containing reagent than the disulfide containing reagent.

In the most preferred embodiments for the refolding of recombinant neurotrophic proteins, the final refolding mixture is deaerated, and refolding is allowed to occur in an anaerobic condition. In addition, in the most preferred embodiments of the present invention, the NGF solution is substantially purified from other proteins prior to refolding. By substantially purified in this context, it is meant that the solution is substantially free of host cell proteins that interfere with the rate or efficiency of NGF refolding. And finally, in preferred embodiments of the invention glycol containing reagents are also included in the refolding mixture.

These procedures are mild and should not result in the chemical modification of the neurotrophic protein. If urea is used as a denaturant in the protocol, it is important to remove any cyanate that may form, by passing the urea solution over an anion exchange column, such as DOWEX 1-X8(BioRad). If cyanate is not removed, it can modify amino groups in the protein (Stark 1967 *Methods in Enzymology* 11:125).

The optimal concentration and choice of denaturant, oxidizing reagent, thiol reagents and their concentrations in the final refolding solution are determined experimentally by monitoring the proportion of neurotrophic protein properly refolded and biologically active. The objective in the final refolding solution is to provide a controlled environment in which disulfide interchange and conformational changes can occur in the neurotrophic protein until the favored conformation and disulfide boding pattern is achieved. The preferred conditions for optimal refolding as set forth above are expected to be substantially the same for all members of the NGF/BDNF family of neurotrophic proteins, since they are closely related in amino acid sequence, including the relative location of all six cysteine residues in the mature protein, and, therefore, presumably assume the same disulfide bonding pattern.

The refolding embodiments of the present invention allow for the expression of neurotrophic proteins in a desireable expression system which has been shown not to yield biologically active neurotrophic proteins. Following the procedures of the present invention the bacterially expressed recombinant neurotrophic protein will attain at least 10% biological activity. In a more preferred embodiment the neurotrophic protein will attain at least 30% biological activity. In the most preferred embodiments the protein will be at least 50% biologically active.

Example 3 below describes an experiment showing that this refolding protocol is successful for refolding mature NGF produced in bacteria as follows:

(1) Correctly folded and fully-biologically active mature NGF, either produced in a eukaryotic cell expression system or purified from natural sources, is denatured and disulfide bonds reduced, as described above, causing a loss of biological activity. Since the NGF was biologically active before denaturation and reduction, it is possible to demonstrate the denaturation and refolding has occurred by the loss of biological activity; (2) The denatured and reduced NGF is renatured according to the protocol described herein to determine that biological activity has been restored. It is presumed that restoration of biological activity is dependent on proper refolding and renaturation of the denatured and reduced protein. It is asserted that mature NGF from any of the sources indicated above, including a bacterial cell expression system, would be structurally indistinguishable after denaturation and reduction. Therefore, successful refolding of denatured and reduced mature NGF from either a eukaryotic cell expression system or from natural sources, indicates that mature NGF produced in bacterial cells can be successfully refolded (see Example 3 and FIG. 3).

Example 3B describes the successful refolding of mature NGF produced in a bacterial expression system using *E.*

*coli*, using methods similar to those described above. The refolded NGF is fully biologically active and migrates at the position of native, insect cell-produced NGF on reversed-phase high performance liquid chromatography.

5. Purification of the Recombinant Neurotrophic Protein

The protocol described above to refold and renature the mature neurotrophic protein may be applied at a stage during purification of the recombinant protein which is most convenient and which has been determined by experience to produce a high yield of biologically active protein.

In one embodiment of the present invention, recombinant members of the NGF/BDNF family may be purified from extracts of the expression host cell by standard techniques of protein chemistry until the recombinant protein is sufficiently pure to be used in pharmaceutical preparations. Such purity is defined as at least 90% of all proteins in the preparation being the neurotrophic protein, and preferably at least 95% of all of the proteins being the neurotrophic protein. In a preferred embodiment the procedures to be used for purification of the recombinant protein may include, but are not limited to, some or all of the following: ion exchange chromatography (e.g., Q-, S-, and DEAE-Sepharose ion exchange columns), gel permeation chromatography (e.g. Superose sizing columns), chromatofocusing (e.g. Mono-P columns), hydrophobic interaction chromatography (e.g., octyl- and phenyl-Sepharose HIC columns), affinity chromatography (e.g., zinc, copper, and mercury metal-affinity columns).

6. Formulation of Pharmaceutical Products

As indicated previously, the neurotrophic proteins of the present invention are contemplated for use as therapeutic agents and thus are to be formulated in pharmaceutically acceptable carriers. In one embodiment of the present invention, the neurotrophic proteins may be chemically modified to improve the pharmacokinetic properties of the molecules. An example would be the attachment of high molecular weight polymeric materials, such as polyethylene glycol, to the neurotrophic protein. The neurotrophic proteins may be administered separately, in combination with other members of the NGF/BDNF family of neurotrophic proteins, or in combination with other neurotrophic proteins or other therapeutic agents, depending on the type of nerve cell disorder being treated.

The therapeutic composition of the present invention is preferably administered parenterally by injection or intrathecally by continuous infusion from an implanted pump. Also, other effective administration forms, such as parenteral slow-release formulations, inhalant mists, orally active formulations, or suppositories, are also envisioned. Our preferred carrier is physiological saline solution, but it is contemplated that other pharmaceutically acceptable carriers may also be used. In one preferred embodiment it is envisioned that the carrier and the neurotrophic protein constitute a physiologically-compatible, slow-release formulation. The primary solvent in such a carrier may be either aqueous or non-aqueous in nature. In addition, the carrier may contain other pharmacologically-acceptable excipients for modifying or maintaining or maintaining the pH, osmolarity, viscosity, clarity, color, sterility, stability, rate of dissolution, or odor of the formulation. Similarly, the carrier may contain still other pharmacologically-acceptable excipients for modifying or maintaining the stability, rate of dissolution, release, or absorption of the neurotrophic protein. Such excipients are those substances usually and customarily employed to formulate dosages for parenteral administration in either unit dose or multi-dose form or for intrathecal delivery by continuous or periodic infusion from an implanted pump or intrathecally by periodic injection.

Once the therapeutic composition has been formulated, it may be stored in sterile vials as a solution, suspension, gel, emulsion, solid, or dehydrated or lyophilized powder. Such formulations may be stored either in a ready to use form or requiring reconstitution immediately prior to administration. The preferred storage of such formulations is at temperatures at least as low as 4° C. and preferably at −70° C. It is also preferred that such formulations containing neurotrophic protein are stored and adminstered at or near physiological pH. It is presently believed that storage and administration in a formulation at pH below approximately pH 5.5 and above approximately pH 8.0 is undesirable.

Preferably, the manner of parenterally administering the formulations containing neurotrophic protein is via a subcutaneous or intramuscular route. To achieve the desired dose of neurotrophic protein, repeated daily or less frequent subcutaneous or intramuscular injections may be administered. It is believed that the administration of neurotrophic protein in daily doses below approximately 0.01 mg/kg may not be effective, while the administration of daily doses of greater than 1 mg/kg have undesirable side effects. It is also contemplated that certain formulations containing neurotrophic protein are to be adminstered orally. Preferably, neurotrophic protein which is adminstered in this fashion is encapsulated. The encapsulated neurotrophic protein may be formulated with or without those carriers customarily used in the compounding of solid dosage forms. Preferably, the capsule is designed so that the active portion of the formulation is released at that point in the gastro-intestinal tract when bioavailability is maximized and pre-systemic degradation is minimized. Additional excipients may be included to facilitate absorption of neurotrophic protein. Diluents, flavorings, low melting point waxes, vegetable oils, lubricants, suspending agents, tablet disintegrating agents, and binders may also be employed.

Regardless of the manner of administration, the specific dose is calculated according to the approximate body weight of the patient. Further refinement of the calculations necessary to determine the appropriate dosage for treatment involving each of the above mentioned formulations is routinely made by those of ordinary skill in the art and is within the ambit of tasks routinely performed by them without undue experimentation. In bio-tests, no toxic effects are observed using the neurotrophic proteins of this invention.

EXAMPLE 1

Isolation, Sequencing and Expression of the Human Gene for BDNF

A. Use of the Polymerase Chain Reaction to Amplify Portions of the Human BDNF Gene.

The following oligonucleotides were synthesized based on the reported nucleic acid sequence for pig BDNF (Leibrock et al. 1989 ibid.):

BDNF-1 [non-degenerate, sense strand oligo located immediately upstream of the fifth coding base in pig BDNF, also containing a 5' BamHI site]

5' GGA TCC GGT GAG AAG AGT GAT GAC 3'

BDNF-2 [partially degenerate guessmer, sense strand oligo running downstream from the initiation codon for pig BDNF; this oligo was synthesized in two different pools to reduce degeneracy; a guessmer is an oligonucleotide whos degeneracy has been reduced by using mammallian codon usage preferences]

BDNF-2A

5' ATG ACN ATC/A/T CTG TTT/C CTG ACN ATG 3'

BDNF-2B

5' ATG ACN ATC/A/T CTG TTT/C CTC ACN ATG 3'

BDNF-3 [non-degenerate, anti-sense strand oligo located immediately downstream of the termination codon for pig BDNF, also containing a 5' SpeI site]
5' ACT AGT TAA TCT ATA CAA CAT AAA GCC 3'
BDNF-4 [partially degenerate guessmer, anti-sense strand oligo running upstream from the termination codon for pig BDNF]
5' ATN GTG/C AGN GTA/G CAN ACA/G CA 3'
BDNF-5 [degenerate, sense strand oligo located in the coding region for the mature (processed) BDNF protein]
5' GAT/C AAA/G AAA/G ACN GCN GTN GAT/C ATG 3'

PCR reactions were performed using human genomic DNA as template and the following combinations of synthetic oligonucleotides as primers: BDNF-1 and BDNF-3; BDNF-2A and BDNF-3; BDNF-2B and BDNF-3; BDNF-2A and BDNF-4; BDNF-2B and BDNF-4; and, BDNF-1 and BDNF-4. The reaction products were electrophoresed and DNA (Southern) blots were probed with radiolabeled BDNF-5 to identify amplified fragments likely to correspond to human BDNF. See Experimental Appendix in this Example for details.

There were bands at approximately the expected size that hybridized to BDNF-5 in the reactions using BDNF-1/BDNF-3, BDNF-2A/BDNF-3, and BDNF-2B/BDNF-3 as primers. The DNA at the position of the hybridizing Southern band from the electrophoresed BDNF-1/BDNF-3 reaction mixture was cut out of the gel and an aliquot was sequenced directly using BDNF-1 and BDNF-3 as sequencing primers to give a partial sequence of the human gene in the coding region for BDNF (FIG. 1). The remainder of this amplified DNA was subcloned into SmaI-cut phage M13mp10 and positive subclones selected based on hybridization to radiolabeled BDNF-5. Two independent positive subclones in opposite orientations, BDNF-PCR1 & 2, were sequenced to give the sequence of the human gene in the coding region for BDNF (FIG. 1).

B. Use of DNA Amplified With PCR to Clone the Human Gene for BDNF.

DNA at the position of the amplified hybridizing Southern band was radiolabeled and used to screen a human genomic DNA library in phage lambda EMBL3 and 6 positive clones were plaque purified. The DNA from clone #3 was digested separately with the following restriction enzymes: HinfI; AluI; RsaI; and, NcoI/Sau3AI. These enzymes were chosen because they break the BDNF coding sequence into several fragments suitable in size for cloning into M13. Restriction fragments containing BDNF coding sequence were subcloned into phage M13mp10 and sequenced to confirm the sequence of the human gene in the region coding for BDNF (FIG. 1). FIG. 1 also shows the inferred amino acid sequence of the precursor and mature (processed) human BDNF protein. The cleavage site proposed in FIG. 1 is based on the similarities of the cleavage sites in the known sequences of NGF and pig BDNF and the known amino acid sequences of NGF and pig BDNF.

The BDNF sequence obtained from PCR amplified fragments (FIG. 1) and from two human genomic DNA clones differed in nucleic acid position 196. The human genomic clone had an A in place of G at position 196, which changes amino acid 66 from valine to methionine. This difference occurs in the precursor, not the mature, biologically-active form of BDNF. This change of a single base pair and a single amino acid may represent an allelic difference in the BDNF sequence within the human genome.

Sequencing of an additional clone gave a sequence identical to that shown in FIG. 1, except that the amino acid at position 223 was lysine (K) instead of arginine (R) and the codon was AAA instead of AGA. This difference occurs in the mature biologically-active active form of human BDNF. This may represent an alternate human allele at this position.

C. Expression of Biologically Active BDNF in COS-7 cells

In order to confirm that the human BDNF gene we obtained actually coded for biologically active BDNF, the gene was expressed transiently in COS-7 cells and the expressed material was assayed for the ability to promote the survival of embryonic day 10 chick dorsal root ganglion neurons in culture, a known property of BDNF purified from pig brains (Barde et al. 1982 *The EMBO Journal* 1:549).

1. Preparation of a DNA Construct for the Expression of Human BDNF

The gel-purified DNA containing the human BDNF coding sequence, as prepared in Part B, above, amplified from human genomic DNA by PCR with oligonucleotides BDNF-1 and BDNF-3 was ligated into the COS cell expression vector pSG5 (Green et al. 1988 *Nuc. Acids Res.* 16:369). Plasmid pSG5 was digested with restriction endonucleases EcoRI and BamHI and the cohesive ends were made blunt by treatment with the Klenow fragment of DNA polymerase I in the presence of all four deoxyribonucleotides. The gel-purified DNA containing the entire BDNF coding sequence was then ligated into the blunt-ended pSG5. The orientation of inserted DNA in which the BDNF precursor protein can be expressed from the SV40 immediate early promoter upon transfection into COS cells was identified by restriction mapping. In the desired orientation, the BDNF insert can be separated from the vector following digestion with BamHI and BglII.

2. Transfection of COS Cells

DNA from pSG5 with and without the BDNF coding insert was prepared by the method of alkaline lysis followed by CsCl density centrifugation (Maniatis et al., ibid.). The plasmid DNA was transfected into COS-7 cells using lipofectin according to protocol C of the manufacturer's instructions (BRL). COS cell cultures transfected with plasmid DNA without a BDNF coding insert served as a negative control.

3. Bioassay of Expressed Materials

Figure 8:
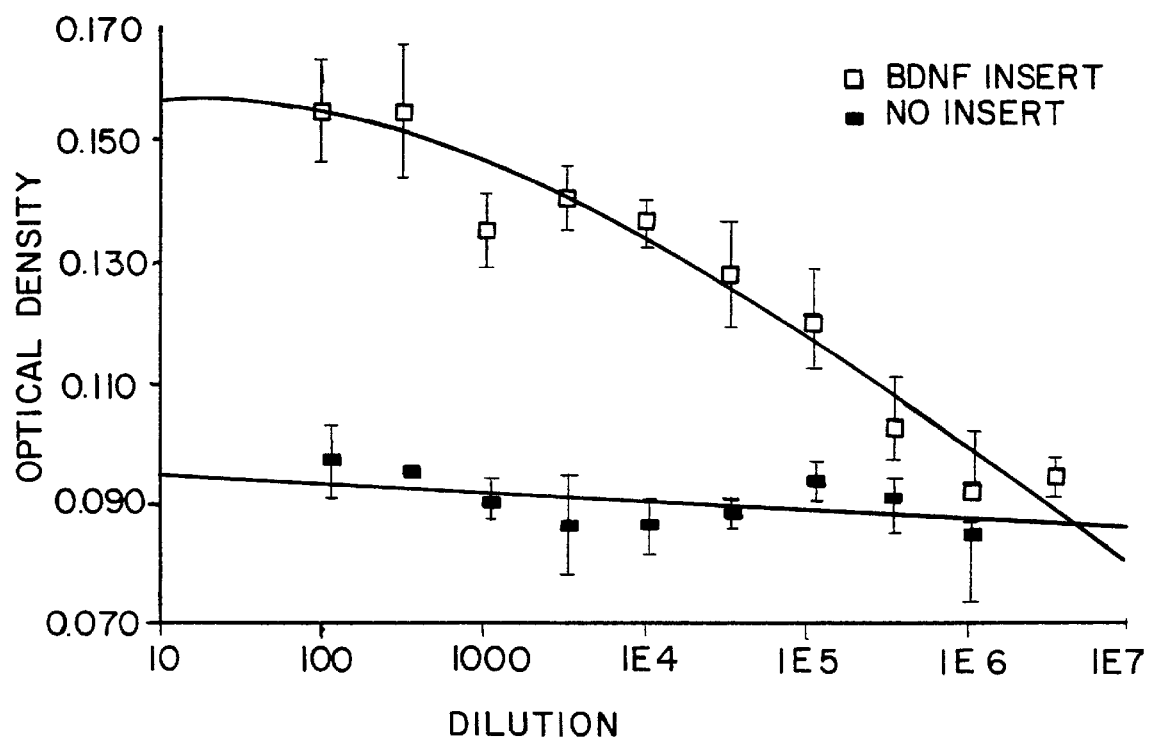
FIG. 8 depicts the bioassay using E10 chick dorsal root ganglion neurons of extracts of COS-7 cells transfected with plasmid pSG5 with and without a human BDNF insert.

Twenty-four hours after transfection the cells were scraped off the dish and harvested by brief centrifugation. Cell pellets were extracted by brief sonication on ice in 20 mM sodium phosphate, pH 6.7 containing 1 mM EDTA, 0.1 mM PMSF, and 0.1 $\mu$M pepstatin. Serial dilutions of the cell extract from each culture were assayed for bioactivity using chick embryo day 10 dorsal root ganglion neurons (see Experimental Appendix to Example 3). There was significant biological activity detected in the extract of cells transfected with pSG5 containing the BDNF insert, but not in the extract of cells transfected with pSG5 without an insert (FIG. 8). These results indicate that the gene we have cloned is capable of expressing a biologically active BDNF.

D. Expression of Mature Human BDNF in *E. coli.*

The human mature BDNF gene, as described in FIG. 1, is inserted into *E. coli* expression vectors, such vectors are introduced into *E. coli* host cells, and expression of the gene to produce human mature BDNF is accomplished according to the procedures described in Example 2 below by replacing the BDNF gene for the NGF gene.

Experimental Appendix to Example 1

1. Molecular biology methods

The polymerase chain reaction (PCR) was performed essentially as described in Saiki et al, 1988 *Science* 239: 487. PCR reaction products were electrophoresed through 2% agarose gels and transferred onto Zeta-Bind membranes (BioRad) for DNA (Southern) blotting. Appropriate amplified bands were cut from original gels and prepared for subcloning by repairing the ends with the Klenow fragment of DNA polymerase (New England Biolabs) and then either cloned blunt-ended or, if restriction sites were placed in the primers, cloned after digestion with the appropriate enzymes. Such fragments were subcloned into appropriately cut and phosphatased M13mp10 vector (Amersham). Oligonucleotides were radiolabeled by kinasing (T. Maniatis, E. F. Fritsch, J. Sambrook, *Molecular Cloning: A Laboratory Manual* (Cold Spring Harbor Laboratory, Cold Spring Harbor, N.Y., 1982)). Oligonucleotide hybridization conditions were 6×SSCP, 2×Denhardt's, 2 mM EDTA, 0.05% sodium pyrophosphate, 0.1% SDS, 100 mcg/ml yeast tRNA as non-specific competitor, pH 8.0. The temperature of hybridization and the stringency conditions for washing hybridized blots and filters were adjusted individually for each oligonucleotide probe based on its relative GC content. Long, radiolabeled DNA probes were prepared by random priming [A. P. Feinberg and B. Vogelstein, *Anal. Biochem.* 132, 6 (1983)]. Hybridization conditions using such probes were: 5×SSCP, 2×Denhardt's, 2 mM EDTA, 0.05% sodium pyrophosphate, 0.1% SDS, 250 µg/ml herring sperm DNA, pH 8.0 at 65° C.; washing at 65° C. in 0.1×SSCP and 0.1% SDS. Sequencing was done by the dideoxy chain termination method [F. Sanger, S. Nicklen, A. R. Coulson, *Proc. Natl. Acad. Sci. U.S.A.* 74, 5463 (1977)] using as template single-stranded DNA prepared from subclones in both orientations in M13 vectors.

EXAMPLE 2

Production of Recombinant NGF in *E. Coli*

A synthetic gene encoding the mature (processed) form of human NGF was purchased from British Biotech. This gene is identical to the human nucleic acid sequence reported for NGF (Ullrich et al. 1983 ibid.), except for changes in the human nucleic acid sequence made to insert a variety of restriction sites and is supplied in the plasmid BBG26.

The plasmid was transformed into *E. coli* strain DH5alpha to produce the plasmid in sufficient quantity for subsequent operations. In order to modify this synthetic gene for insertion into an appropriate expression vector, the following two oligonucleotides were synthesized:

```
NGF-A
              Translational
       BamHI     Coupler
5'-GATC   CGATCTTGGAGGATGATTAA ATG TCC TCC TCC CAC CCG ATC
TTT CAC CGC GGC G-3'

NGF-B
    EcoRI
5'-AAT TC GCC GCG GTG AAA GAT CGG GTG GGA GGA GGA CAT
TTAATCA TCCTCCAAGATCG-3'
```

These oligonucleotides contain a BamHI site at the 5' end and an EcoRI site at the 3' end. There is a unique EcoRI site located near the 5' end of the synthetic NGF gene. After exposure of BBG26 to the restriction enzyme EcoRI, the synthetic oligonucleotide can be ligated to the cut plasmid just 5' of the EcoRI site, thus replacing the 5' portion of the NGF coding sequence. This replacement of the 5' end of the coding sequence allows the insertion of an upstream translational coupler (see above oligonucleotide sequences) and the substitution of codons preferred by *E coli*. (according to deBoer and Kastelein in *From Gene to Protein: Steps Dictating the Maximal Level of Gene Expression* (1986) Davis and Reznikoff, eds. pp. 225–283, Butterworths, N.Y.). These changes are designed to promote efficient expression of the NGF sequences.

The oligonucleotide NGF-A and NGF-B were kinased and annealed together then ligated to the EcoRI-cut and phosphatased plasmid BBG26 and the mixture phosphatased. The mixture was treated with the restriction enzyme BamHI and the approximately 390 bp BamHI fragment containing the modified NGF coding sequence was gel purified. This fragment was ligated to each of two different gel-purified, BamHI-cut, and phosphatased *E. coli* expression vectors: (1) a vector based on a T7 phage promoter system, called pT5T; or, (2) a vector based on a hybrid 'Tac' promoter derived from both the tryptophan and lactose, called pT3XI-2 (see Experimental Appendix to this Example and FIGS. 4 & 5 for details). This resulted in the formation of either pT5T:NGF or pT3XI-2:NGF.

pT5T:NGF was transformed into *E. coli* strain BL21 (DE3). This strain (described in Studier and Moffat *J. Mol. Biol.* (1986) 189:113–130) contains the T7 RNA polymerase gene under control of the IPTG inducible lac promoter on a nonexcisable lysogenic lambda bacteriophage. Since the insert in the pT5T vector is under control of the T7 phage promoter, this ultimately places expression of the inserted sequences under control of the lac promoter, hence expression is inducible by isopropyl β-D-thiogalatopyranoside (IPTG). Transformants were picked, grown up, and hybridized with the $^{32}$P-labeled 390-bp BamHI fragment to determine which transformants carried the NGF insert. Eight positives were selected, grown up, and vector DNA was isolated and sequenced. Each of the eight carried the correct insert in the correct orientation in the vector. Two were grown up separately in Luria broth containing 15 mcg/ml tetracycline to an optical density (O.D.) of ca. 0.6, then the cultures were induced by addition of 1 mM final concentration of IPTG. Samples of each culture were taken at intervals from 2 to 21 hr after induction and lysed in SDS-PAGE sample buffer (0.025% bromphenol blue, 10% glycerol, 1% β-mercaptoethanol, 2% SDS, 0.0625M Tris-HCl, pH 6.8). Each sample was electrophoresed by reducing SDS-PAGE and production of NGF monitored both by the appearance of a Coomassie-brilliant-blue-stained band at the correct molecular weight and by Western blot analysis using antibody to mouse submaxillary gland NGF (Sigma). As negative controls, samples were taken from identical cultures not induced and from cultures of bacteria transformed with the pT5T vector not containing the NGF insert. The results shown in FIG. 2 indicate that transformant pT5T:NGF-18 produces a protein band at the molecular weight expected for processed NGF that is also recognized by anti-NGF antiserum (lanes labeled: pT5T:NGF-18 2,4,6, 8,10, and 21 hrs of induction with IPTG). As expected, this band is not detectable in bacteria transformed with pT5T without the NGF insert (lanes labeled: pT5T u (uninduced) and i (induced)) or in pT5T:NGF-18 not induced by the presence of IPTG (lane labeled: pT5T:NGF-18 0 hours of induction with IPTG).

pT3XI-2:NGF was transformed into a phage-resistant E. coli K-strain, JM107. Thirteen transformants were grown up as for pT5T:NGF transformants and 3 were found to express the human mature NGF protein by SDS-PAGE of cell extracts after both staining with Coomassie Brilliant Blue and immunostaining with anti-mouse NGF antiserum as above for pT5T:NGF transformants.

Amino-terminal amino acid sequence of the recombinant NGF produced by pT3XI-2:NGF in E. coli JM107 indicated that the amino-terminal methionine had been removed during expression in at least 85% of the NGF produced. This indicates that the NGF being produced has the correct amino-terminus for processed mature human NGF.

The NGF produced as described herein was found to have no detectable biological activity as determined by the procedures set forth in Example 3 below.

The protein produced by either vector pT5T:NGF or vector pT3XI-2:NGF was tested for nerve growth stimulating activity and recombinant hβNGF produced in insect cells using a baculovirus vector was used as a control. The positive control gave half-maximal neuronal survival at a concentration of 1.1 mg/ml. In contrast, the polypeptides produced in E. coli from the two vectors both demonstrated no significant biological activity, even at a concentration of approximately 3,600 mg/ml.

Experimental Appendix to Example 2

1. Description of pT5T, an expression vector based on the "T7 promoter" system (Please refer to FIG. 4 for features of the vector)

The T7 promoter based expression vector pT5T is essentially the same as pJU1003 [Squires, et. al., J. Biol. Chem. (1988) 263:16297–16302], except that there is a short stretch of DNA between the unique BglII site 5' to the T7 promoter and the ClaI site in the tetracycline resistance gene. The sequence of this DNA is:

```
ClaI
ATCGATGATA AGCTGTCAAA CATGAGAATT GAGCTCCCCG
GAGATCCTTA GCGAAAGCTA AGGATTTTTT TTAGATCT
                                   BglII
```

2. Description of pT3XI-2: a modification of pKK223-3 using a hybrid 'Tac' promoter system (Please refer to FIG. 5 for features of the vector)

The starting plasmid for this construction was plasmid pKK223-3 purchased from Pharmacia. Plasmid pKK223-3 carries a partial gene for tetracycline resistance. This nonfunctional gene was replaced by a complete tetracycline resistance gene carried on plasmid pBR322. Plasmid pKK223-3 was digested completely with SphI and partially with BamHI. A 4.4 kilobase pair fragment was gel purified and combined with a synthetic adaptor with the sequence:

```
5'    GATCTAGAATTGTCATGTTTGACAGCTTATCAT    3'
3'        ATCTTAACAGTACAAACTGTCGAATAGTAGC 5'
``` and a 539 base pair fragment of DNA from a Cla I, Sph I digest of the tetracycline resistance gene of pBR322 (PL Biochemicals, catalog number 27-4891-01). The resulting plasmid was designated pCJ1.

Next a XhoI linker purchased from New England Biolabs was inserted into plasmid pCJ1's PvuII site to form plasmid pCJX-1. This insertion disrupts the rop gene which controls plasmid copy number. An EcoRI fragment containing the lac 1 gene was purified from plasmid pMC9 [Calos, et al., Proc. Natl. Acad. Sci. USA (1983), 80:3015–3019] then inserted into the XhoI site with XhoI to EcoRI adapters having the sequence:

```
5'    TCGAGTCTAGA         3'
3'         CAGATCTTTAA     5'
```

The polylinker sequence between the EcoRI and Pst I sites in plasmid pCJX-1 was next replaced with a polylinker sequence shown here:

```
5'    AATTCCCGGG TACCAGATCT GAGCTCACTA GTCTGCA    3'
3'         GGGCCC ATGGTCTAGA CTCGAGTGAT CAG       5'
```

The plasmid vector so obtained is designated pCJXI-1.

Finally, the tetracycline resistance gene was replaced with a similar gene which had the recognition sites for restriction enzymes Hind III, Bam HI, and Sal I destroyed by bisulfite mutagenesis. The following procedure was used to mutate the tetracycline resistance gene of pBR322. Plasmid pBR322 was cut with Hind III, then mutagenized with sodium bisulfite [Shortle and Nathans, Proc. Natl. Acad. Sci. USA (1978) 5:2170–2174]. The mutagenized DNA was ligated to form circular DNA, then cut with Hind III to linearize any plasmid that escaped mutagenesis. E. coli JM109 [Yanisch-Perron, et al., Gene (1985) 33:103–119] was transformed with the plasmid, then plated on selective media. Plasmids were isolated from tetracycline resistance colonies and checked for loss of the Hind III site in the tetracycline resistance gene. The successfully mutated plasmid was designated pT1. A similar procedure was followed to mutagenize the Bam HI site in pT1, yielding plasmid pT2. Plasmid pT2 in turn was mutagenized to remove the Sal I site, forming plasmid pT3. A ClaI/BsmI fragment of pT3 carrying the mutated tetracycline resistance gene was isolated and used to replace the homologous fragment of pCJXI-1 to form pT3XI-2. The mutated tetracycline resistance gene still encodes a functional protein.

3. Formation of pT3XI-2-φ10TC3FGFsyn (preparing the tac promoter vector for NGF)

Initially a "gene" for basic Fibroblast Growth Factor (bFGF) was synthesized. This "gene" codes for the same sequence as that reported for bFGF by Sommer et al.(1987 Biochem. Biophys. Res. Commun. 141:67) but uses the codons that are found preferably in highly expressed genes in E. coli. The structure of this gene is such that the coding portion is preceded by a translational coupler sequence (see Squires, et al., 1988, ibid.) to ensure efficient initiation of translation.

The bFGF synthetic gene was first inserted into vector M13mp18 between the EcoRI and Hind III sites and sequenced. The structure of this gene is:

```
AATTCAGGA TCCGATCGTG GAGGATGATT AAATGGGTAC CATGGCTGCT GGCTCCATCA
        GTCCT AGGCTAGCAC CTCCTACTAA TTTACCCATG GTACCGACGA CCGAGGTAGT
EcoRI   BamHI         RBS               FGFstart
                                  Translational Coupler 3

CTACCCTGCC GGCACTGCCG GAAGACGGTG GCTCCGGTGC TTTCCCGCCG GGCCACTTCA
GATGGGACGG CCGTGACGGC CTTCTGCCAC CGAGGCCACG AAAGGGCGGC CCGGTGAAGT
```

```
AAGACCCGAA ACGTCTGTAC TGTAAAAACG GTGGCTTCTT CCTGCGTATC CACCCGGATG
TTCTGGGCTT TGCAGACATG ACATTTTTGC CACCGAAGAA GGACGCATAG GTGGGCCTAC

GTCGTGTCGA CGGCGTACGT GAAAAAAGCG ACCCGCACA  TCAAACTGCA GCTGCAGGCTG
CAGCACAGCT TGCCGCATGC ACTTTTTTCC TGGGCGTGT  AGTTTGACGT CGACGTCCGAC

AAGAACGTG  GTGTTGTATC TATCAAAGGC GTTTGCGCAA ACCGTTACCT GGCTATGAAAG
TTCTTGCAC  CACAACATAG ATAGTTTCCG CAAACGCGTT TGGCAATGGA CCGATACTTTC

AAGACGGTC  GTCTGCTGGC TAGCAAATGT GTAACTGACG AATGTTTCTT CTTCGAACGTC
TTCTGCCAG  CAGACGACCG ATCGTTTACA CATTGACTGC TTACAAAGAA GAAGCTTGCAG

TGGAAAGCA  ACAACTACAA CACCTACCGT TCTCGTAAAT ACACTTCTTG GTACGTTGCTC
ACCTTTCGT  TGTTGATGTT GTGGATGGCA AGAGCATTTA TGTGAAGAAC CATGCAACGAG

TGAAACGTA  CCGGCCAGTA CAAACTGGGT TCCAAAACTG GCCCGGGTCA GAAAGCAATCC
ACTTTGCAT  GGCCGGTCAT GTTTGACCCA AGGTTTTGAC CGGGCCCAGT CTTTCGTTAGG

TGTTCCTGC  CGATGAGCGC TAAATCTTAA ACTAGTA
ACAAGGACG  GCTACTCGCG ATTTAGAATT TGATCATTCGA
                               FGFstop   HindIII
```

Certain features of the gene are highlighted.

It was then isolated by digestion with Bam HI and Hind III and inserted into Bam HI/Hind III-cut pJU1003 (Squires, et al., 1988, ibid.) yielding pJU1003-synFGF. This plasmid was cut with Xba I and Hind III and the Xba I/Hind III fragment carrying the bFGF gene was isolated. This fragment was ligated into pT3XI-2 cut with EcoRI and Hind III, using an EcoRI-XbaI linker:

```
5' ATT TCC ACA ACG GTT TCC CT        3'
3'         GG TGT TGC CAA AGG GAG ATC 5'
```

The new plasmid is designated pT3XI-2-φ10TC3FGFsyn.

4. Inserting NGF expression construct into the Tac promoter vector pT3XI-2-φ10TC3FGFsyn was cut with BamHI, which resulted in the linearization of the 7.4-kb pair expression vector and the release of the ca. 0.5-kb pair bFGF DNA fragment. The 390-bp BamHI fragment containing the modified NGF coding sequences was ligated into the gel purified Bam HI-cut vector DNA fragment, resulting in the plasmid pT3XI-2:NGF.

EXAMPLE 3
Refolding and Renaturation of Members of the NGF/BDNF Family of Neutrophic Proteins A. The Refolding of Mature NGF Produced in Eukaryotic Cells or Purified from Natural Sources One embodiment of the present invention involves the ability to refold and restore biological activity to the inactive, mature form of recombinant NGF produced in bacteria. To demonstrate that this is possible, it was first established that fully biologically active, mature NGF, produced in a eukaryotic cell expression system or purified from natural sources, can be successfully refolded after its biological activity has been destroyed by denaturation and reduction of disulfide bonds. This demonstration is significant for two reasons:

(1) It is reasonable to propose that after being fully denatured and reduced, mature NGF produced in bacteria (originally inactive), or purified from natural sources (originally active), will be inactive and structurally indistinguishable. Since they are indistinguishable structurally, successful refolding of denatured and reduced mature NGF from eukaryotic cells or natural sources indicates that mature NGF expressed from bacteria, after being denatured and reduced, can also be successfully refolded.

(2) The full-length NGF precursor cannot be proteolytically processed in bacteria to produce the correct mature NGF, as it is in eukaryotic cell expression system. Therefore, in bacteria it is necessary to express the coding sequence for mature NGF directly and not that for the full-length precursor. It is theoretically possible that the proper folding and assumption of biological activity of mature NGF will only occur if it is first synthesized as the full-length precursor, as occurs in eukaryotic cells and in natural sources. This would eliminate any likelihood of successfully refolding the mature protein produced in bacteria. However, successful refolding of denatured and reduced mature NGF, as demonstrated herein, proves that proper refolding does not depend on the full-length precursor.

Figure 3:
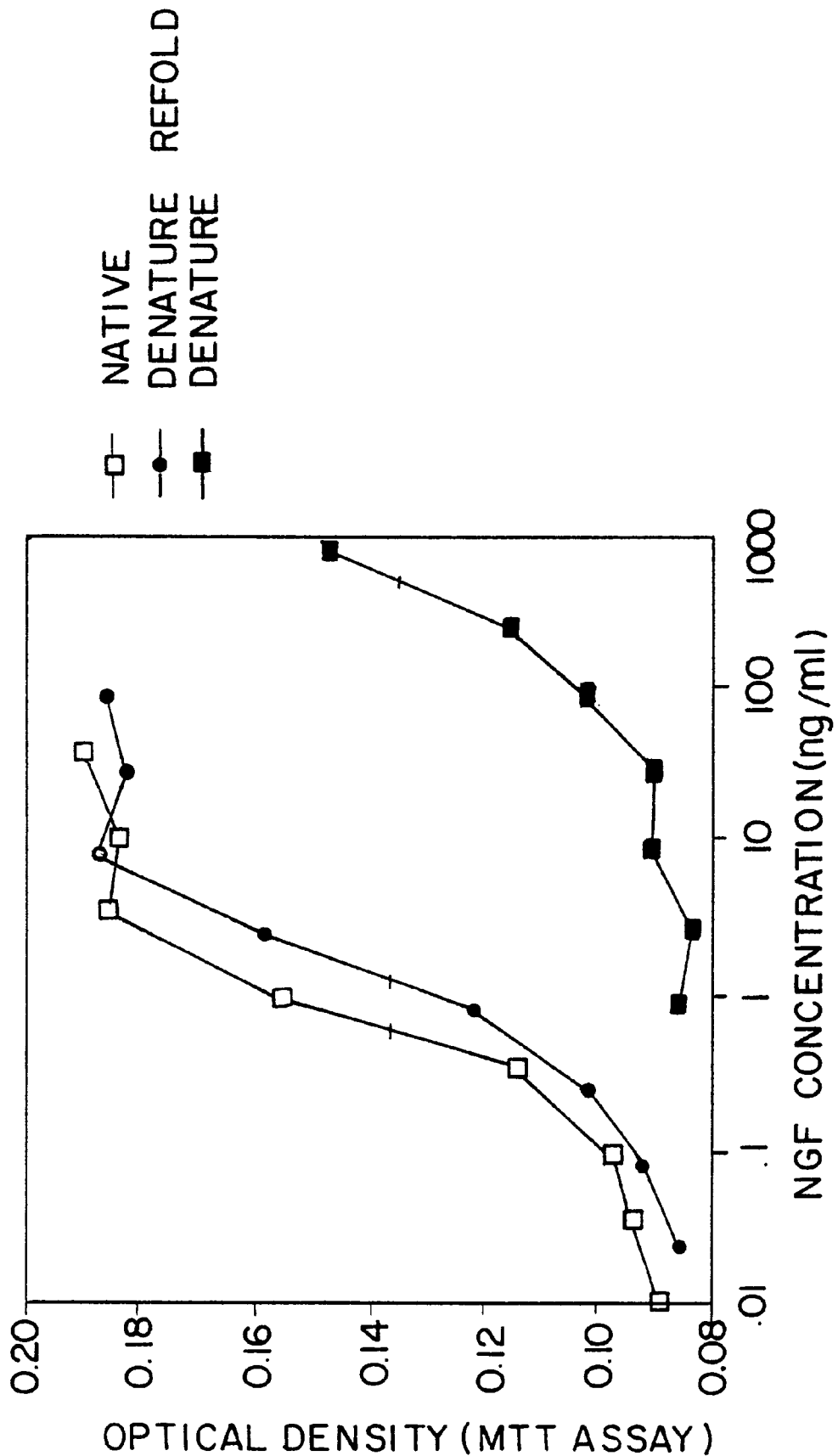
FIG. 3 depicts the loss and regaining of biological activity upon denaturation and refolding, respectively, of mature human NGF produced in eukaryotic cells.

Two forms of originally biologically active, mature NGF were successfully refolded after being denatured and reduced: (1) mature (beta) NGF purified from male mouse submaxillary gland (SIGMA), and (2) recombinant human mature NGF produced in eukaryotic cells according to procedures described in European Patent Publication EP 89113709. FIG. 3 demonstrates that the recombinant human mature NGF produced as above promotes the survival of chick embryo sympathetic ganglion neurons at the concentrations expected for NGF (Greene 1977 Develop. Biol. 58:96–113). FIG. 3 also demonstrates that this biological activity is lost after denaturation and reduction of disulfide bonds. FIG. 3 further demonstrates that full biological activity is restored to the denatured and reduced protein after it is refolded according to the procedures described herein. Essentially similar results were obtained using mature beta-NGF purified from mouse submaxillary gland. These successful refoldings indicate strongly the feasibility of refolding mature NGF produced in bacteria.

1. Protocol for Refolding NGF

NGF was dissolved at a concentration of 0.5 mg/ml in PBS (0.15M NaCl, 0.04M $K_2HPO_4$, 0.02M $KH_2PO4$, pH7.2) and denatured by addition of guanidine hydrochloride to a final concentration of 3M. After 30 minutes at 25° C., dithiothreitol (DTT) was added to a final concentration of 5.6 mM and incubation was continued at 25° C. for another 2 hours (50 mM DTT has also been used with about equal success). Oxidized glutathione was then added to a final concentration of 50 mM and incubated at 25° C. for 10 minutes. This solution was diluted 7-fold in 0.6% Tris (Boehringer/Mannheim 604-205), not pH adjusted, containing 0.2% human serum albumin. L-cysteine was added to a final concentration of 20 or 30 mM with about equal success. This refolding mixture was incubated at 25° C. for 16–20 hours, then the material was concentrated with a Centricon-10 concentrator (Amicon) and the buffer exchanged with PBS.

2. Assay of NGF Biological Activity After Refolding

Untreated starting NGF, NGF left in the denaturing buffer containing 3M guanidine and 5.6 mM DTT, and denatured then refolded NGF were assayed for their ability to promote the survival of neurons from dissociated E11 chick embryo lumbar sympathetic chain ganglia, as described in the Experimental Appendix to this Example. FIG. 3 shows the results of this bioassay. The denatured and reduced NGF exhibited half-maximal biological activity at 450 ng/ml, whereas the starting NGF and the refolded NGF exhibited half-maximal biological activity at 0.5 and 1.0 ng/ml, respectively. These results indicate that denaturation and chemical reduction lowered the biological activity of recombinant human mature NGF by a factor of roughly 1,000 and that the refolding procedure restored to this material the biological activity found in the starting NGF within the roughly 2-fold experimental error of the bioassay.

B. The Refolding of Mature Human NGF Produced in *E. coli* Cells

Mature NGF expressed in *E. coli* cells as described in Example 2 above is biologically inactive. Such NGF is refolded to produce biologically active NGF according to the procedures described below.

1. Preparation of the Starting Material for Refolding 10 grams *E. coli* cell paste from pT3X1-2:NGF in JM107 as described in Example 2 was resuspended in 50 ml of 10 mM EDTA, pH 7.0, and run through a French pressure cell twice at 16,000 psi. The cell extract was spun down at 16,000 xg for 20 minutes and the supernatant was discarded. The pellet was homogenized in 100 ml of 10 mM EDTA, pH 7.0. The resuspended pellet was centrifuged as above and the supernatant discarded. The pellet was again homogenized in 100 ml of 10 mM EDTA, pH 7.0. The resuspended pellet was centrifuged as above and the supernatant discarded. The pellet was homogenized with 30 ml of 4 M urea in 50 mM Tris, pH 8.0, and 0.2% β-mercaptoethanol. The resuspended pellet was spun down and the supernatant discarded, as above. The pellet was homogenized with 30 ml of 20 mM sodium citrate, pH 3.0, containing 8 M urea. The resuspended pellet was spun down as above and the supernatant place on ice. The pellet was homogenized in 30 ml of 20 mM sodium citrate, pH 3.0, containing 8 M urea, centrifuged as above and the supernatant placed on ice. The supernatants may be stored at −80° C.

2. Refolding of the *E. Coli* Extract

To the final supernatant extract described above is added one-fourth volume of 1 M Tris, pH 8.5, containing 8 M urea. Dithiothreitol is added to a final concentration of 5–15 mM and the solution placed at 25° C. for 1 hour. Then cystine (or oxidized glutathione) is added to a final concentration of 15–50 mM and the solution placed at 25° C. for 10–15 minutes. Nine volumes of 100 mM $Na_2HPO_4$, pH 8.3, containing 3.2–4.2 M urea is added followed by cysteine at 2–3 times the final concentration of cystine (or glutathione). The solution is held at 4° C. overnight. These conditions do not reduce or denature active NGF.

The preceding conditions provide ranges of concentrations and alternate reagents that we have found acceptable. The following provides an example of a representative refolding experiment:

Forty ml of the *E. coli* extract described above (containing approximately 650 μgm/ml of NGF as estimated by laser densitometry of coomassie brilliant blue-stained SDS-polyacrylamide gels) received 10 ml of 1 M Tris, pH 8.5, containing 8 M urea. Two ml of 400 mM dithiothreitol was added and the solution placed at 25° C. for 1 hour. Four ml of 600 mM oxidized glutathione was added and the solution placed at 25° C. for 15 minutes, at which time 450 ml of 100 mM $Na_2HPO_4$, pH 8.3, containing 3.2 M urea was added, followed by 6 ml of 1 M cysteine. The solution was placed at 4° C. for 16 hours. This solution is referred to below as the final refolding mixture.

2a. Alternative Methods for Extracting and Refolding Mature Human NGF Produced in *E. Coli*

The following methods are preferable to those already presented, since they result in a significantly greater efficiency and rate of refolding and give higher yields of properly-refolded and biologically-active mature, human NGF.

NGF Extraction

The *E. coli* cells producing NGF (described in Example 2) were broken open by a French press or Gaulin mill in 10 volumes/wt (e.g., 1 liter/100 gm cell paste) of 10 mM EDTA, pH 7.0. The lysate was centrifuged at 16,000×g for 20 minutes to separate supernatant from pellet. The pellet was re-extracted twice more by homogenization in 10 volumes of 10 mM EDTA, pH 7.0 and centrifuged as above. The pellet was extracted once again as above. The washed pellet was extracted with 5 volumes/wt of 20 mM Tris, pH 8.0 containing 2 M urea and centrifuged as above. The supernatant was discarded.

NGF was extracted from the pellet with 10 volumes/wt of 20 mM citrate, pH 3.0 containing 8 M urea and centrifuged as above. The supernatant was retained on ice while the pellet was re-extracted for the last time with 4 volumes/wt of 20 mM citrate, pH 3.0 containing 8 M urea, as above. The NGF was about 50% of the total protein in the CU (citrate urea) extract.

A typical refold was performed as follows: 20 ml 1 M Tris, pH 8.5 containing 8 M urea was added to 80 ml of the CU extract containing about 2 mg/ml NGF. Dithiothreitol or 2 β-mercaptoethanol was added to 5 mM final concentration and the mixture was held at 25° C. for 30–60 minutes. Then oxidized glutathione or cystine was added to 20 mM final concentration and the reaction mixture was held at 25° C. for 10–15 minutes. Next 19 volumes of diluting buffer (100 mM $Na_2HPO_4$, 10 mM ethanolamine, pH 8.3, 4.6 M urea, and 15.8% polyethylene glycol 300) was added. Cysteine or 2-mercaptoethylamine was added to 3 mM final concentration. The final refolding mixture was deaerated under vacuum and flushed with purified argon through 3–5 cycles of deaeration and argon purging. The mixture was sealed against gas entry and held under argon at 9° C. for 1–7 days.

It is advisable to optimize the ratio of cysteine (or 2-mercaptoethylamine) to oxidized glutathione (or cystamine) in the final refolding mixture. The optimal ratio (typically between 2–10) can vary depending upon several factors, including the temperature at which the final reaction mixture is held. Temperatures of 0–25° C. yield refolded NGF; however, the preferred temperature is between 4–9° C. The dilution step yields refolded NGF at final dilutions of 3× to 80×; however, dilutions of 20× or greater give the highest percentage of total NGF that becomes refolded. Polyethylene glycols 200, 300, and 1000 yield refolded NGF when used up to 25% final concentration; however, the yield is greater with polyethylene glycol 200 or 300 at 15% final concentration. Ethylene glycol, glycerol, propylene glycol can be used in place of polyethylene glycol; however, the efficiency of refolding is reduced approximately two-thirds compared to polyethylene glycol 300. The concentration of urea in the final refolding mixture can be between 4 to 6 M, although 4.5–6.0 M gives the highest yields of refolded NGF. Refolding occurs over a pH range from 8 to 10 in the final refolding mixture, although pH 10 gave the fastest rate of refolding. The phosphate buffer concentration in the final refolding mixture is best maintained between 100 to 300 mM, while keeping the ratio of phosphate buffer to ethanolamine at 10:1.

Refolding performed as above typically results in greater than about 30% of the initial amount of NGF attaining the properly-refolded biologically-active form. If the NGF extracted from *E. coli* is denatured and reduced in urea and mercaptoethanol as above and then purified over RP-HPLC (emerging as a single peak at about 43% acetonitrile), the refolding efficiency increases to greater than 60% of the starting NGF. This indicates that contaminants in the *E. coli* extract partially interfere with the efficiency of refolding. Purification of the NGF before refolding by means other than RP-HPLC, such as ion-exchange chromatography, may also increase the efficiency of refolding.

3. Determination of the Efficiency of Refolding

The total amount of NGF in a final refolding mixture was determined as follows: Laser densitometry scans were performed after coomassie brilliant blue staining of SDS-polyacrylamide gels run under reducing conditions in which some lanes contained different concentrations of an NGF calibration standard (the baculovirus, insect cell-produced material described in Example 3) while some lanes contained aliquots of the final refolding mixture. By establishing the quantitative relationship between the laser densitometry optical density and the amount of NGF standard protein, one can determine the amount of NGF in an unknown sample.

The amount of properly refolded NGF in a final refolding mixture was determined as follows: Serial dilutions of the final refolding mixture were tested for their ability to promote the survival of chick embryo sympathetic chain neurons in vitro in the assay described in the Experimental Appendix to Example 3. In the same assay, a range of concentrations of the standard insect cell-produced NGF were also tested for their ability to promote neuronal survival. The dilution of final refolding mixture that gave half-maximal survival in the bioassay was considered to contain the same concentration of properly refolded NGF as the concentration of standard NGF needed to give half-maximal survival.

These methods were used to determine the amount of properly refolded NGF in the experimental refolding described above. In the bioassay, 3.7 ng/ml of insect cell-produced NGF was required to give half-maximal survival. Since a dilution of 1:1500 of the final refolding mixture gave half-maximal survival, it was concluded that the final refolding mixture contained (1500×3.7=) 5550 ng/mL of active NGF. The total amount of NGF in the final refolding mixture was estimated by laser densitometry to be 52000 ng/ml, indicating a refolding efficiency of approximately 11%.

Figure 9:
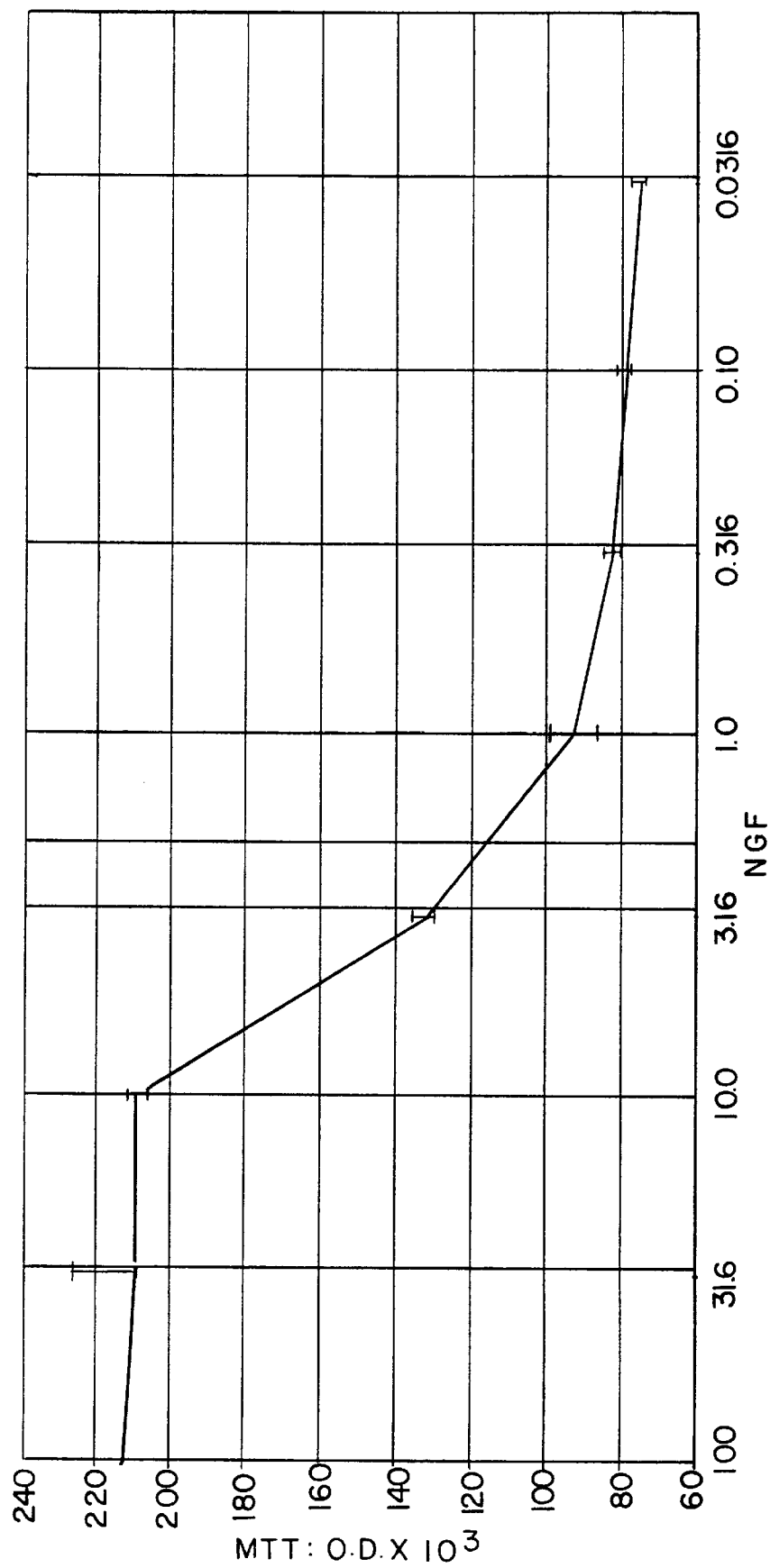
FIG. 9 depicts a dose-response curve for insect cell-produced human recombinant NGF using the bioassay on E11 chick embryo sympathetic ganglion neurons.
Figure 10:
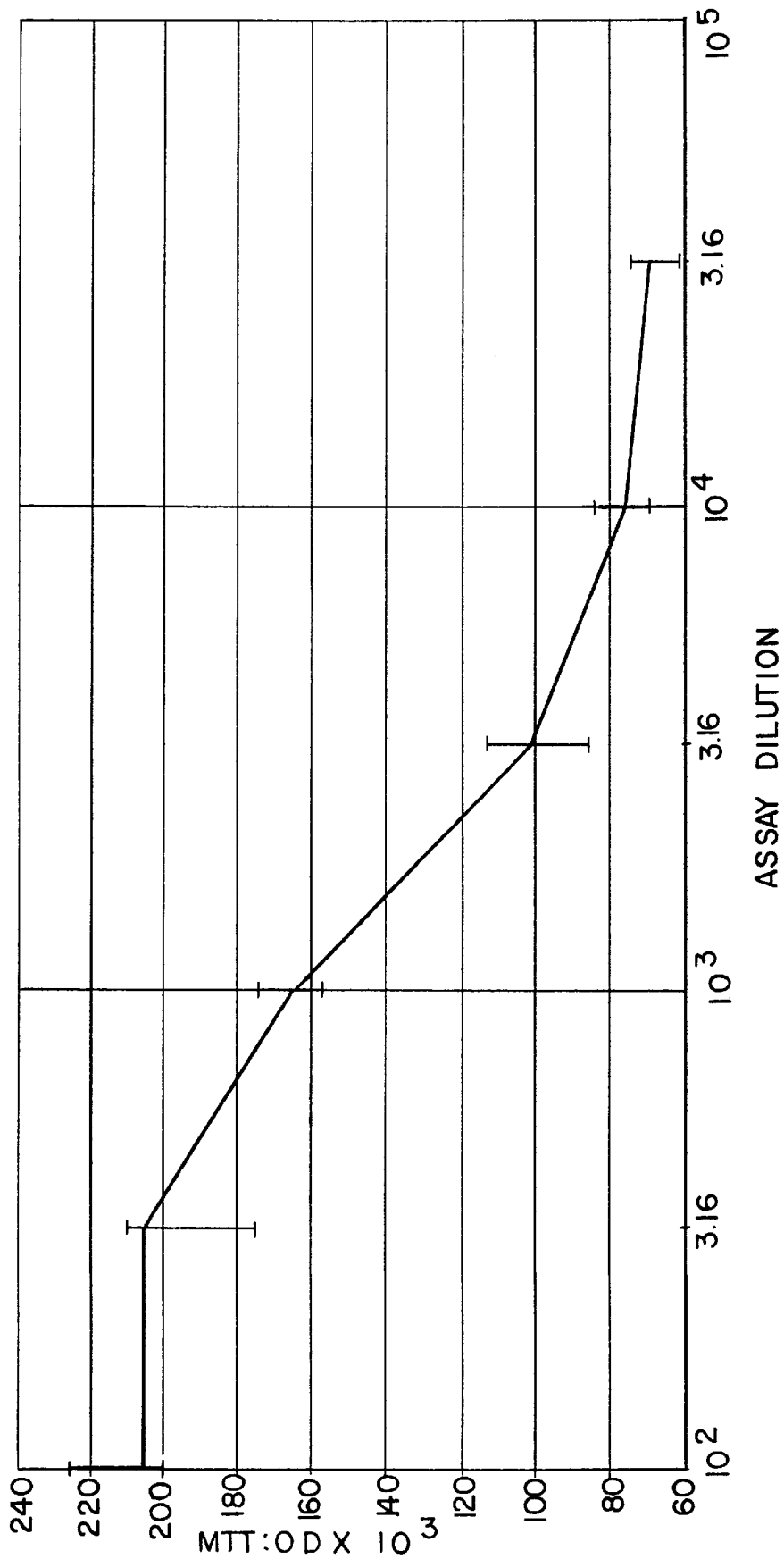
FIG. 10 depicts the bioactivity of serial dilutions of the final refolding mixture of E. coli-produced human recombinant NGF using the bioassay on E11 chick embryo sympathetic ganglion neurons.

FIG. 9 illustrates the bioassay results for the standard insect cell-produced NGF, which gave half-maximal survival at 3.7 ng/ml. FIG. 10 illustrates the bioassay results for the final refolding mixture, which gave half-maximal survival at a dilution of 1:1500.

4. Purification and Characterization of Refolded NGF Produced in *E. Coli*

Reversed-phase high performance liquid chromatography (RP-HPLC) was used to purify and characterize the biologically active, refolded NGF in the final refolding mixture. The RP-HPLC conditions were as follows: solvent A=0.1% trifluoroacetic acid (TFA) in water; solvent B=0.1% TFA in acetonitrile (all HPLC grade reagents); column=VyDec C4 #214TP54; flow rate=1 ml per minute. The sample is injected at time 0 and the gradient developed with the following program:

| Time | % B |
|---|---|
| 0 | 5% |
| 5–10 | 5–20% |
| 10–40 | 20–50 |
| 40–50 | 50–80% |

The positions at which native NGF and reduced NGF were determined in order to calibrate the column for subsequent analysis of refolded samples. % B is the amount of Solvent B in the column eluent. A sample of insect cell-produced, native NGF eluted at approximately 34% B. A sample of denatured and reduced insect cell-produced NGF eluted at approximately 43% B. The NGF was denatured and reduced by exposure to 6 M guanidine hydrochloride and 50 mM dithiothreitol in 200 mM Tris, pH 8.5. Individual RP-HPLC columns required separate calibration with these standards to determine the exact % B at which these two samples eluted.

Figure 11A:
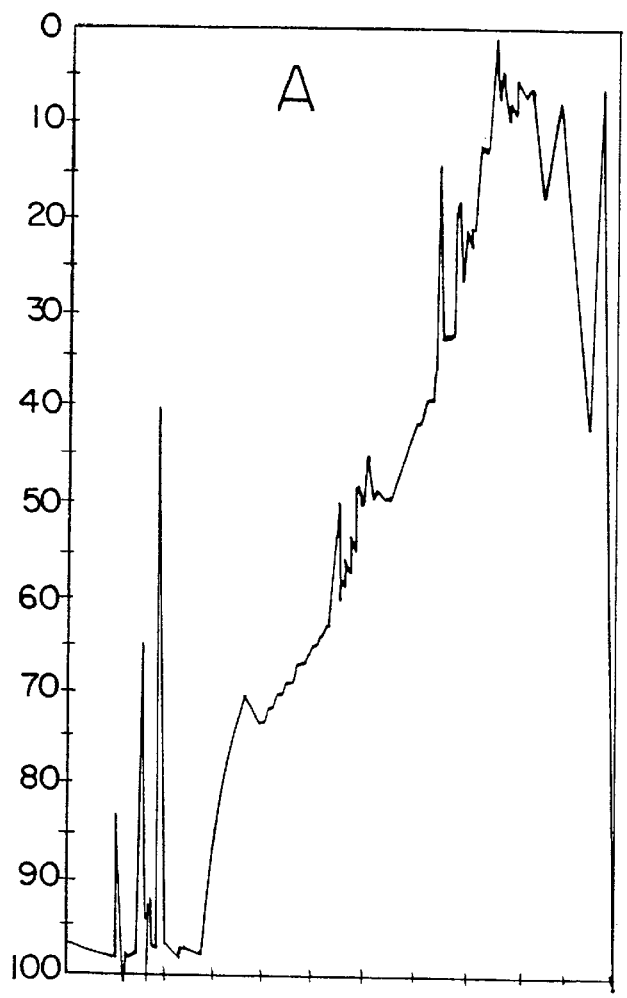
FIG. 11A and 11B depicts the analysis on reversed-phase high performance liquid chromatography of (A) 50 µl of the final refolding mixture assayed in FIG. 10 to which 100 ng of native, insect cell-produced NGF has been added, and (B) 50 µl of the final refolding mixture to which no native, insect cell-produced NGF has been added. The position at which native, insect cell-produced NGF normally runs on this column has been indicated by the label NGF followed by an arrow.
Figure 11B:
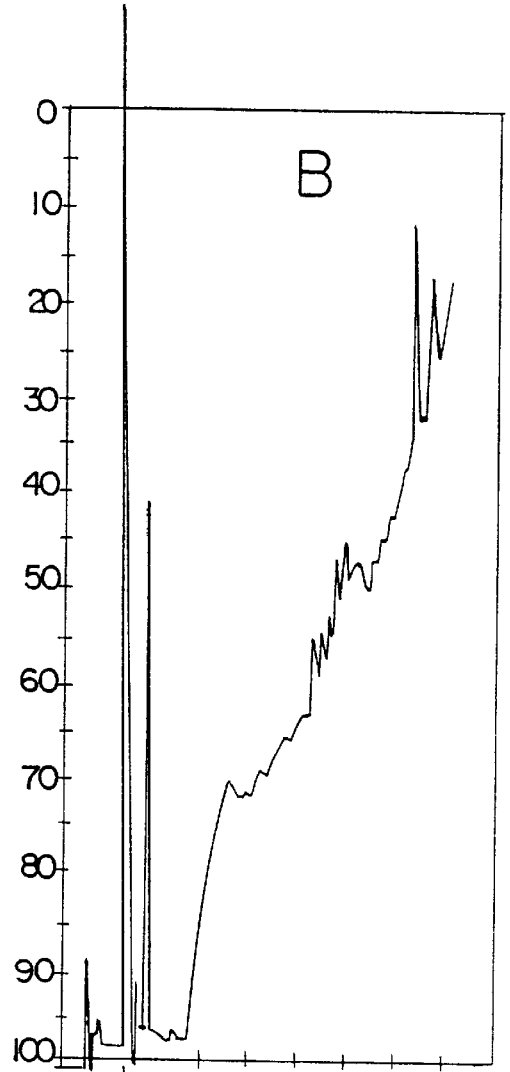

In 50 $\mu$l of the final refolding mixture from the experimental refolding described above, a peak of protein appeared at the position of native NGF (FIG. 11B). No protein ran at this position before refolding. When 100 ng of native insect cell-produced NGF was added to a second 50 $\mu$l sample, the size of the peak at the position of NGF approximately doubled (FIG. 11A). This confirmed that the protein that appeared after refolding ran at the same position as native NGF and also indicated that there was approximately 100 ng of this material in 50 $\mu$l of the final refolding mixture. Only this peak exhibited detectable bioactivity when fractions collected from across the RP-HPLC gradient were assayed for bioactivity in the sympathetic neuron survival assay. This further confirms the identity of this protein in the final refolding mixture as NGF. The specific activity of this peak was within the range of that observed for native insect cell-produced NGF (half-maximal survival at 0.5–5 ng/ml in separate assays on different days). Thus the refolded NGF from *E. coli* runs at the position of native insect cell-produced NGF and is fully biologically active.

When refolding is performed as in Example 3.B.2a. above, purification of the refolded NGF can be accomplished as follows. The final refolding mixture is concentrated about 20-fold using a concentrating device such as a hollow-fiber filter/concentrator. The concentrate is then dialyzed against 10–20 volumes of urea-containing buffer. The buffer used is 50 mM sodium acetate, pH 5.0, since the refolded NGF is soluble and stable in this buffer and the pH is appropriate for subsequent cation exchange chromatography. The dialysis buffer includes sufficient urea so that the final urea concentration after dialysis is 1.5–2 M. This allows *E. coli* proteins and improperly refolded NGF to precipitate, as judged by reversed-phase HPLC.

The dialyzed sample is centrifuged to pellet the precipitate and then applied to S-Sepharose in 50 mM Na acetate, pH 5.0. The column is washed and eluted with a linear salt gradient of 0.05–1.5 M NaCl. The NGF is purified to homogeneity by reversed-phase HPLC.

Figure 12:
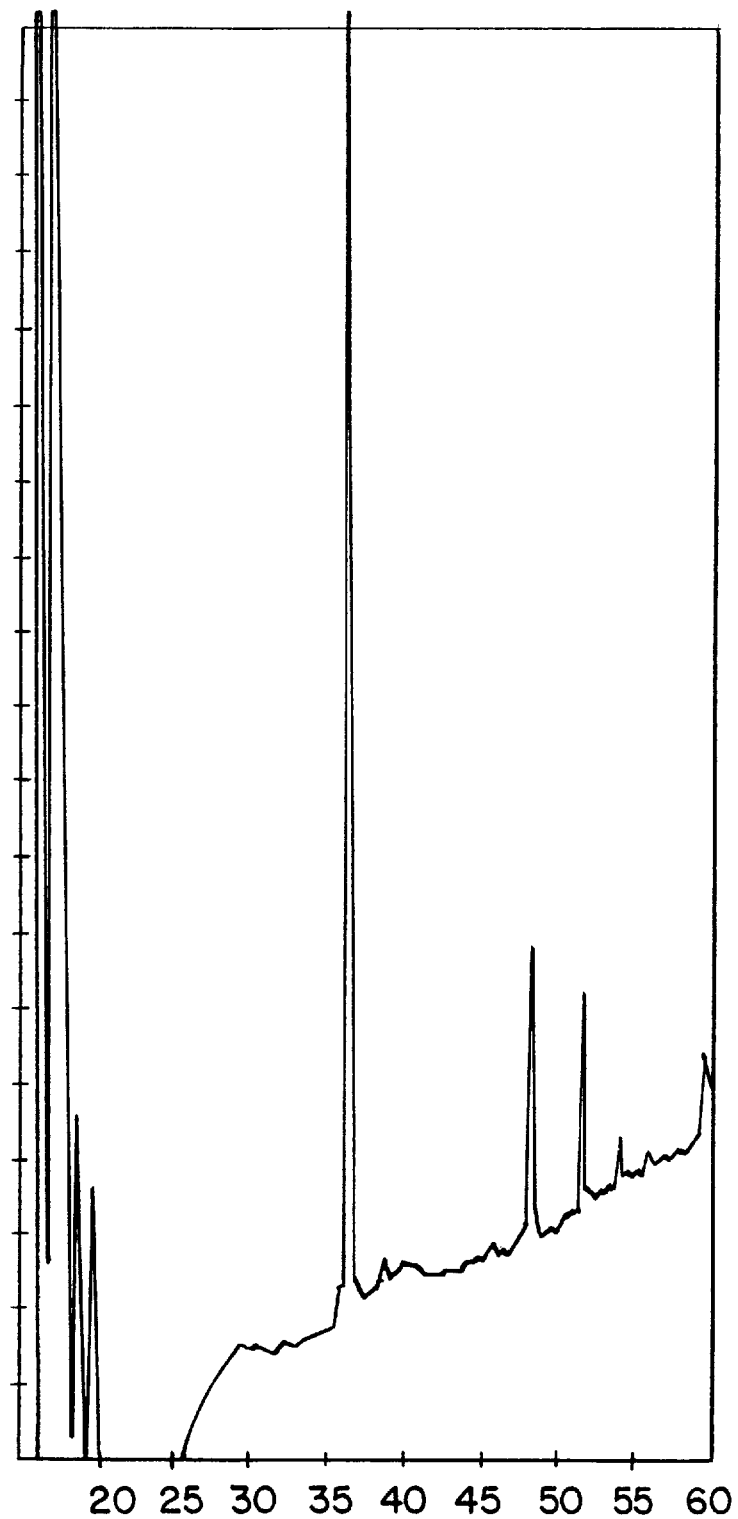
FIG. 12 depicts the elution profile of proteins (Optical Density at 214 nm) when the final refolding mixture before further purification is chromatographed on a C4 column by reversed-phase HPLC. Properly refolded NGF is the largest protein peak, eluting at approximately 37% acetonitrile.
Figure 13:
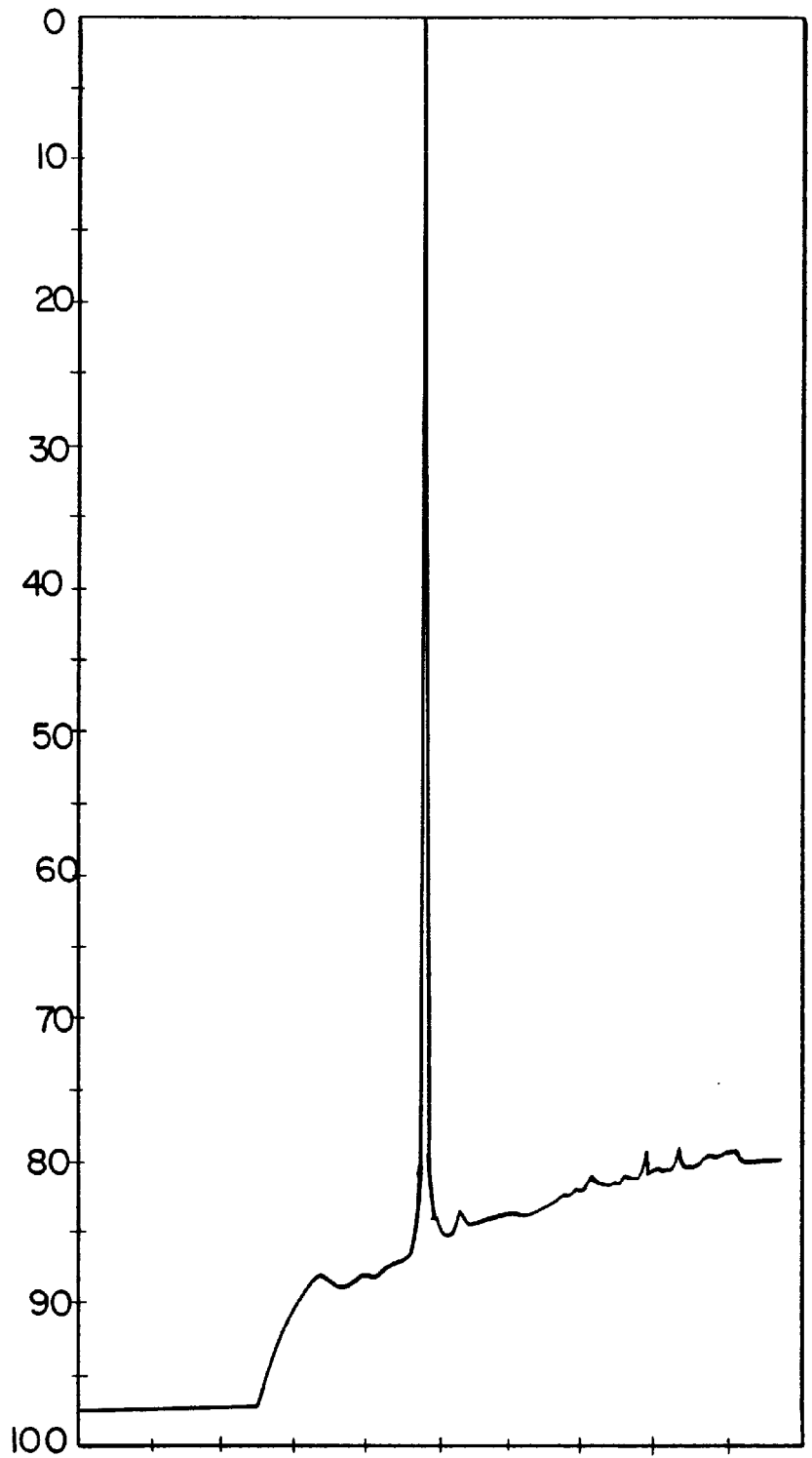
FIG. 13 depicts the elution profile of proteins (Optical Density at 214 nm) when the final refolding mixture after dialysis and concentration but before S-Sepharose is chromatographed on a C4 column by reversed-phase HPLC. Properly refolded NGF is the largest protein peak, eluting at approximately 37% acetonitrile.
Figure 14:
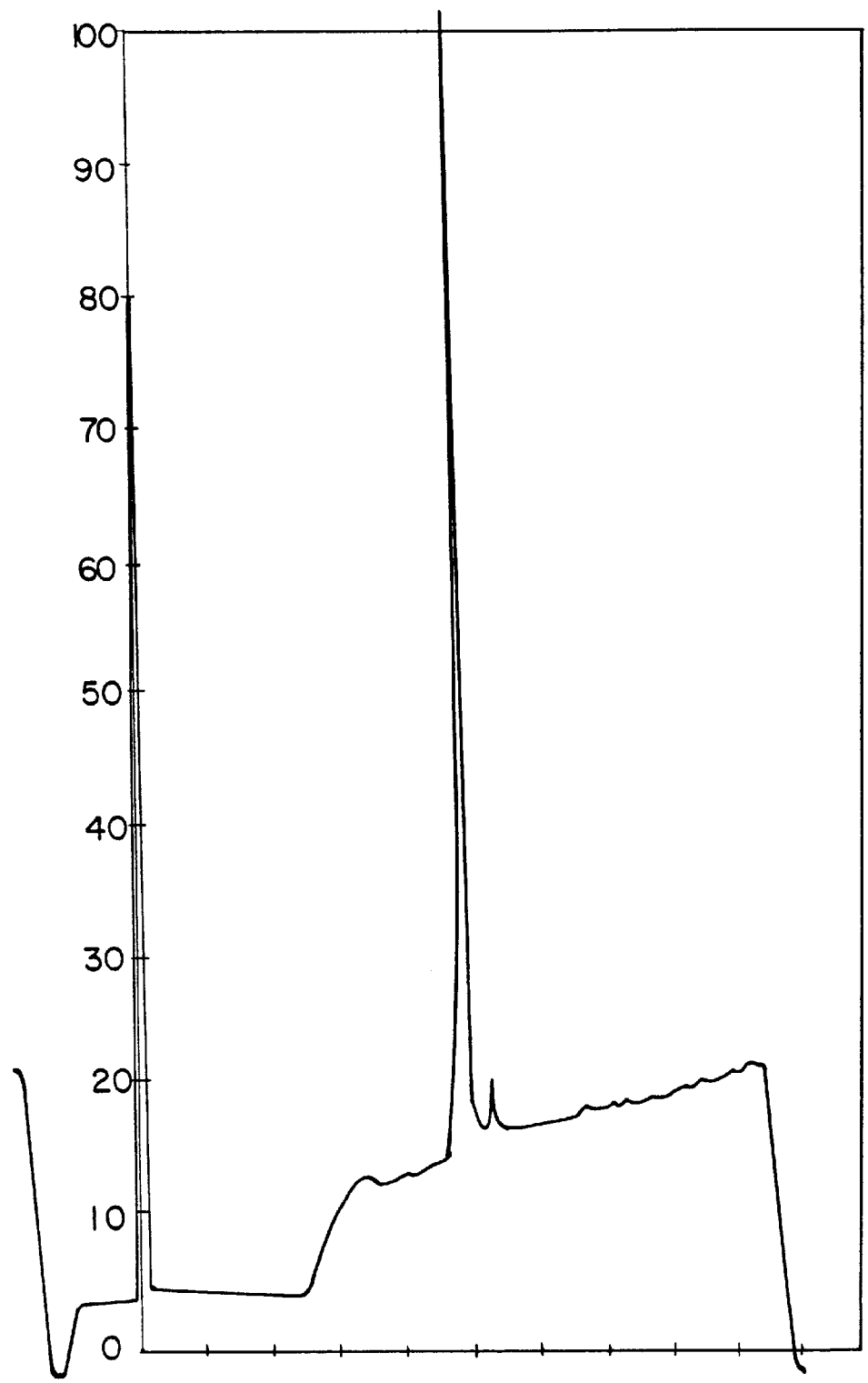
FIG. 14 depicts the elution profile of proteins (Optical Density at 214 nm) when the final refolding mixture after purification over S-Sepharose is chromatographed on a C4 column by reversed-phase HPLC. Properly refolded NGF is the largest protein peak, eluting at approximately 37% acetonitrile. The small protein peak eluting immediately after the main peak, is the monomeric form of properly refolded NGF that is formed during chromatography on reversed-phase HPLC.

FIG. 12 illustrates the reversed-phase HPLC (RP-HPLC) protein profile of the final refolding mixture. The properly-refolded NGF is the major protein peak, eluting at about 37% acetonitrile. FIG. 13 illustrates the RP-HPLC protein profile of the final refolding mixture after concentration and dialysis, but before chromatography over S-Sepharose. Contamination with the other proteins visible in FIG. 12, including non-refolded NGF eluting at about 47% acetonitrile (FIG. 12), has been significantly reduced and properly-refolded NGF is substantially pure. FIG. 14 illustrates the RP-HPLC protein profile of the material after chromatography over S-Sepharose. Almost all contaminating proteins have been removed. The small peak that elutes just after the major peak of refolded NGF is the monomeric form of refolded NGF. The major peak eluting at about 37% acetonitrile is the dimeric form of refolded NGF.

The specific activity of the reversed-phase-purified NGF in the chicken embryo sympathetic nerve cells survival bioassay was $E.D._{50}=0.17\pm0.01$ ng/ml. For comparison, the specific activity of human recombinant NGF produced in insect cells (as described in Example 3) was $E.D._{50}= 0.26\pm0.02$ ng/ml. This demonstrates that the refolded NGF, produced in *E. coli* and refolded and purified by the methods just described, is fully biologically active.

C. The Refolding of Mature Human BDNF

Mature human BDNF recombinantly produced in *E. Coli*, as described in Example 1D above, is made biologically active by refolding according to the procedures described in Example 3B. above.

D. The Refolding of Mature NGF-3

Mature human NGF-3, as described in Example 4 below, is made biologically active by refolding according to the procedures described in Example 3B. above.

Experimental Appendix to Example 3

1. Bioassay of NGF and BDNF

Cultures of chick embryo sympathetic chain and dorsal root ganglia were prepared as previously described (Collins and Lile 1989 *Brain Research* 502:99). Briefly, sympathetic or dorsal root ganglia were removed from fertile, pathogen-free chicken eggs that had been incubated for 8–11 days at 38° C. in a humidified atmosphere. The ganglia were chemically dissociated by exposure first to Hanks' Balanced Salt Solution without divalent cations, containing 10 mM HEPES buffer pH 7.2 for 10 min at 37° C., then by exposure to a solution of 0.125% bactotrypsin 1:250 (Difco, Detroit, Mich.) in Hanks' Balanced Salt Solution modified as above for 12 min at 37° C. Trypsinization was stopped by addition of fetal calf serum to a final concentration of 10%. After this treatment, ganglia were transferred to a solution consisting of Dulbeccols high glucose Modified Eagle Medium without bicarbonate containing 10% fetal calf serum and 10 mM HEPES, pH 7.2 and mechanically dissociated by trituration approximately 10 times through a glass Pasteur pipet whose opening had been fire polished and constricted to a diameter such that it took 2 seconds to fill the pipet. The dissociated ganglia were then plated in culture medium (Dulbecco's Modified Eagle Medium supplemented with 10% fetal calf serum, 4 mM glutamine, 60 mg/L penicillin-G, 25 mM HEPES, pH 7.2) in 100 mm diameter tissue culture dishes (40 dissociated ganglia per dish) for three hours. This preplating was done in order to separate the nonneuronal cells, which adhere to the dish, from the nerve cells, which do not adhere. After three hours, the nonadherent nerve cells were collected by centrifugation, resuspended in culture medium, and plated in 50μl per well onto half area 96 well microtiter tissue culture plates at a density of 1500 nerve cells per well. The microtiter wells had been previously exposed to a 1 mg/ml solution of poly-L-ornithine in 10 mM sodium borate, pH 8.4 overnight at 4° C., washed in distilled water, and air dried.

10 μl of a serial dilution of the sample to be assayed for neurotrophic activity was added to each well and the dishes were incubated for 20 hours at 37° C. in a humidified atmosphere containing 7.5% $CO_2$. After 18 hours, 15μl per well of a 1.5mg/ml solution of the tetrazolium dye MTT in Dulbecco's high glucose modified Eagle Medium without bicarbonate containing 10 mM HEPES, pH 7.2 was added and the cultures placed back in the 37° C. incubator for 4 hours. Then, 75 μl of a solution of 6.7 ml of 12 M HCl per liter of isopropanol was added and the contents of each well triturated 30 times to break open the cells and suspend the dye. The absorbance at 570 nm was determined relative to a 690 nm reference for each well using an automatic microtiter plate reader (Dynatech, Chantilly, Va.). The absorbance of wells which had not received any neurotrophic agent (negative controls) was subtracted from the absorbance of sample-containing wells. The resulting absorbance is proportional to the number of living cells in each well, defined as those nerve cells capable of reducing the dye. The concentration of trophic activity in trophic units (TU) per ml was defined as the dilution that gave 50% of maximal survival of nerve cells. For example, if the sample gave 50% maximal survival when diluted 1:100,000 the titer was defined as 100,000 TU/ml. Specific activity was determined by dividing the number of trophic units per ml by the concentration of protein per ml in the undiluted sample.

EXAMPLE 4

Cloning NGF-3, A New Member of the NGF/BDNF Family of Neutrophic Proteins

A. Use of the Polymerase Chain Reaction (PCR) to Amplify a DNA Fragment of NGF-3

Two partially degenerate oligonucleotides, NNF-1 and NNF-3, were synthesized based on highly conserved regions of the nucleic acid sequences encoding the mature (processed) NGFs of various species and pig and human BDNF. The sequences of these oligonucleotides and 5' restriction sites inserted for ease of subcloning amplified fragments are presented below. (I=inosine)

NNF-1 (SENSE STRAND)

```
     HindIII
5'- GGAAGCTT GTG TG(C/T) GAC AG(C/T) (A/G)T(C/T) AG(C/T)
(A/G)(A/T)G TGG GT -3'
```

NNF-3 (ANTI-SENSE STRAND)

```
     BamHI
5'- CCGGATCC TTC CA(A/G) TG(C/T) (C/T)TI (A/G)(A/C)(A/G)
TCI AT(G/C) CC(C/T) C(G/T)G CA-3'
```

NNF-1 and NNF-3 were used as primers in PCR (see Experimental Appendix to Example 1) with human genomic DNA as template. The PCR products were electrophoresed in a 3% agarose gel and a fluorescent DNA band around the expected size of 150–200bp was excised from the gel and cloned by blunt end ligation into SmaI-cut phage M13mp10. The resulting ligation reaction was plated on *E. coli* strain TG1 and duplicate lifts were taken. The first lift was hybridized at high stringency to the randomly-labeled human BDNF coding sequence obtained by PCR (see Example 1). The second lift was hybridized at high stringency to the randomly labeled human NGF mature protein coding sequence obtained from British Biotech (see Example 1). Any plaque that hybridized to either probe was not pursued further. All remaining plaques that contained an insert, as indicated by failure to produce beta-galactosidase, were sequenced. The phage in one such plaque, NNF-18, contained a 136-bp amplified DNA fragment between oligonucleotides NNF-1 and NNF-3 that coded for a protein fragment that is 53% identical to human NGF and 44% identical to human BDNF (FIG. 7). Some amino acid homologies are to both NGF and BDNF and some are unique to NGF or BDNF (FIG. 7). The NGF-3 fragment bears approximately the same homology to NGF or BDNF as the latter two proteins bear to each other (FIG. 7). The DNA sequence of this fragment is underlined in FIG. 6, where it is compared to NGF and BDNF. Based on these homologies, it was concluded that this fragment had been amplified from a gene for a new member of the NGF/BDNF family of neurotrophic proteins. The new gene and protein were named NGF-3.

B. Use of the DNA Amplified With PCR to Clone the Human Gene for NGF-3

The DNA fragment of NGF-3, amplified by PCR as above, was radiolabeled by performing PCR amplification in the presence of $^{32}$P-dCTP and used to screen a human genomic library in lambda FIX II (Stratagene cat. no. 946203). Six positives from $1.2 \times 10^6$ plaques were purified by repeated cloning. Partial digests of the DNA from one positive using the restriction enzyme HinCII were subcloned into vector M13. Several M13 subclones that hybridized to the radiolabeled PCR fragment were sequenced in both orientations according to the procedures described in Example 1B. above, in order to obtain the complete nucleic acid (FIG. 6) and inferred amino acid (FIG. 7) sequences for human NGF-3.

C. Expression of Mature Human NGF-3 in *E. Coli*

The human mature NGF-3 gene obtained as described in Example 4B. above, is inserted into *E. coli* expression vectors, such vectors are introduced into *E. coli* host cells, and expression of the gene to produce mature BDNF is accomplished according to the procedures described in Example 2 above by replacing the NGF-3 gene for the NGF gene. The recombinantly expressed protein is then made biologically active by refolding according to the procedure described in Example 3B above.

The above description and examples set forth a description of the invention and the preferred embodiments thereof. Many modifications of the methods described herein will be obvious to those of ordinary skill in the art and are within the scope of the claims as set forth below.

We claim:

1. A method for folding human mature nerve growth factor (NGF), recombinantly expressed in prokaryotic cells, wherein the protein attains substantially full biological activity which comprises:

(a) dissolving said expressed NGF to a concentration of about 0.6 mg/ml in 20 mM sodium citrate, pH at about 3.0, containing 8 molar urea;

(b) raising the pH of the dissolved solution by addition of a 1M Tris Solution, pH at about 8.5, containing 8M urea;

(c) reducing said NGF by addition of dithiothreitol to a concentration of about 5–15 mM;

(d) oxidizing said NGF by addition of oxidized glutathione or cystine to a concentration of about 15–50 mM;

(e) diluting said solution of NGF about nine fold with a solution of 100 mM, $Na_2HPO_4$, pH at about 8.0, containing about 3.2 to 4.2M urea;

(f) catalyzing disulfide interchange of said NGF by addition of about 2 to 3 fold cysteine relative to the concentration of glutathionine or cystine; and (g) isolating said NGF from said reaction mixture.

2. A method for refolding and renaturing neurotrophic proteins recombinantly expressed in prokaryotic cells, wherein the protein attains substantially full biological activity, wherein said protein is selected from the group consisting of human mature nerve growth factor (NGF), human mature brain derived neurotrophic factor (BDNF), and human mature nerve growth factor 3 (NGF-3); said method comprising:

(a) disrupting all intramolecular and intermolecular disulfide bonds in a solution containing said neurotrophic protein to form free thiols by adding a denaturant and a reducing agent to said solution;

(b) oxidizing said free thiols with a disulfide containing compound to form mixed disulfide bonds;

(c) diluting said solution in the presence of a thiol containing compound; and (d) isolating said neurotrophic protein from said solution.

3. The method of claim 2 wherein said disrupting comprises the steps of:

(a) dissolving said expressed neurotrophic protein to a concentration of about 0.6 mg/ml in 20 mM sodium citrate, pH at 3.0, containing 8 molar urea;

(b) raising the pH of said solution by addition of 1M Tris solution, pH at 8.5, containing 8 molar urea; and (c) reducing said NGF by addition of dithiothreitol to a concentration of about 5–15 mM.

4. The method of claim 2 wherein said disulfide containing compound is oxidized glutathione or cystine.

5. The method of claim 2 wherein said denaturant is guanidine hydrochloride or urea.

6. The method of claim 2 wherein said thiol containing compound is cysteine or dithiothreitol.

7. A method for refolding and renaturing neurotrophic proteins recombinantly expressed in prokaryotic cells, wherein the protein attains substantially full biological activity, wherein said protein is selected from the group consisting of human mature nerve growth factor (NGF), human mature brain derived neurotrophic factor (BDNF), and human mature nerve growth factor 3 (NGF-3); said method comprising:

(a) dissolving said expressed neurotrophic protein to a concentration of about 0.6 mg/ml in 20 mM sodium citrate, pH at 3.0, containing 8 molar urea;

(b) raising the pH of said solution by addition of 1M Tris solution, pH at 8.5, containing 8 molar urea;

(c) reducing said neurotrophic protein by addition of dithiothreitol to a concentration of about 5–15 mM;

(d) oxidizing said neurotrophic protein by addition of oxidized glutathione or cystine to a concentration of about 15–50 mM;

(e) diluting the solution of oxidized neurotrophic protein about nine fold with a solution of 100 mM $Na_2HPO_4$, pH at about 8.0, containing about 3.2 to 4.2M urea;

(f) catalyzing disulfide interchange of said neurotrophic protein by addition of about 2 to 3 fold cysteine relative to the concentration of glutathione or cystine; and (g) isolating said neurotrophic protein from the catalyzed reaction mixture.

8. A method for folding human mature nerve growth factor (NGF), recombinantly expressed in bacteria, wherein the protein attains substantially full biological activity which comprises:

(a) dissolving said bacterial expressed NGF to a concentration of about 0.6 mg/ml in 20 mM sodium citrate, pH at about 3.0, containing 8 molar urea;

(b) raising the pH of the dissolved solution by addition of a 1M Tris Solution, pH at about 8.5, containing 8M urea;

(c) reducing said NGF by addition of dithiothreitol to a concentration of about 5–15 mM;

(d) oxidizing said NGF by addition of oxidized glutathione or cystine to a concentration of about 15–50 mM;

(e) diluting said solution of NGF about nine fold with a solution of 100 mM, $Na_2HPO_4$, pH at about 8.0, containing about 3.2 to 4.2M urea;

(f) catalyzing disulfide interchange of said NGF by addition of about 2 to 3 fold cysteine relative to the concentration of glutathionine or cystine; and (g) isolating said NGF from said reaction mixture.

9. A method for refolding and renaturing neurotrophic proteins recombinantly expressed in bacteria, wherein the protein attains substantially full biological activity, wherein said protein is selected from the group consisting of human mature nerve growth factor (NGF), human mature brain derived neurotrophic factor (BDNF), and human mature nerve growth factor 3 (NGF-3); said method comprising:

(a) disrupting all intramolecular and intermolecular disulfide bonds in a solution containing said neurotrophic protein to form free thiols by adding a denaturant and a reducing agent to said solution;

(b) oxidizing said free thiols with a disulfide containing compound to form mixed disulfide bonds;

(c) diluting said solution in the presence of a thiol containing compound; and (d) isolating said neurotrophic protein from said solution.

10. The method of claim 9 wherein said disrupting comprises the steps of:

(a) dissolving said bacterial expressed neurotrophic protein to a concentration of about 0.6 mg/ml in 20 mM sodium citrate, pH at 3.0, containing 8 molar urea;

(b) raising the pH of said solution by addition of 1M Tris solution, pH at 8.5, containing 8 molar urea; and (c) reducing said NGF by addition of dithiothreitol to a concentration of about 5–15 mM.

11. The method of claim 9 wherein said disulfide containing compound is oxidized glutathione or cystine.

12. The method of claim 9 wherein said denaturant is guanidine hydrochloride or urea.

13. The method of claim 9 wherein said thiol containing compound is cysteine or dithiothreitol.

14. A method for refolding and renaturing neurotrophic proteins recombinantly expressed in bacteria, wherein the protein attains substantially full biological activity, wherein said protein is selected from the group consisting of human mature nerve growth factor (NGF), human mature brain derived neurotrophic factor (BDNF), and human mature nerve growth factor 3 (NGF-3); said method comprising:

(a) dissolving said bacterial expressed neurotrophic protein to a concentration of about 0.6 mg/ml in 20 mM sodium citrate, pH at 3.0, containing 8 molar urea;

(b) raising the pH of said solution by addition of 1M Tris solution, pH at 8.5, containing 8 molar urea;

(c) reducing said neurotrophic protein by addition of dithiothreitol to a concentration of about 5–15 mM;

(d) oxidizing said neurotrophic protein by addition of oxidized glutathione or cystine to a concentration of about 15–50 mM;

(e) diluting the solution of oxidized neurotrophic protein about nine fold with a solution of 100 mM $Na_2HPO_4$, pH at about 8.0, containing about 3.2 to 4.2M urea;

(f) catalyzing disulfide interchange of said neurotrophic protein by addition of about 2 to 3 fold cysteine relative to the concentration of glutathione or cystine; and (g) isolating said neurotrophic protein from the catalyzed reaction mixture.

* * * * *

UNITED STATES PATENT AND TRADEMARK OFFICE
CERTIFICATE OF CORRECTION

PATENT NO. : 5,986,070

DATED : November 16, 1999

INVENTOR(S) : COLLINS ET AL.

It is certified that error appears in the above-identified patent and that said Letters Patent is hereby corrected as shown below:

In column 29, line 30, replace
"5' ATT TCC ACA ACG GTT TCC CT 3'" with
--5' AAT TCC ACA ACG GTT TCC CT 3'--

In column 36, line 2, change "Dulbeccols" to --Dulbecco's--.

In column 38, line 39, change "glutathionine" to --glutathione--.

In column 39, line 55, change "glutathionine" to --glutathione--.

Signed and Sealed this

Twenty-ninth Day of August, 2000

Attest:

Q. TODD DICKINSON

*Attesting Officer*  *Director of Patents and Trademarks*